United States Patent [19]

Urbanek et al.

[11] 4,302,721
[45] Nov. 24, 1981

[54] NON-CONTACTING RESISTIVITY INSTRUMENT WITH STRUCTURALLY RELATED CONDUCTANCE AND DISTANCE MEASURING TRANSDUCERS

[75] Inventors: Karel Urbanek, Atherton; George J. Kren, Los Altos; William R. Wheeler, Saratoga, all of Calif.

[73] Assignee: Tencor Instruments, Mountain View, Calif.

[21] Appl. No.: 39,303

[22] Filed: May 15, 1979

Related U.S. Application Data

[63] Continuation-in-part of Ser. No. 903,493, May 8, 1978, Pat. No. 4,175,441, and a continuation-in-part of Ser. No. 941,233, Sep. 11, 1978, abandoned.

[51] Int. Cl.³ .................... G01N 27/72; G01R 33/12
[52] U.S. Cl. .................................... 324/226; 324/236
[58] Field of Search ............... 324/225, 226, 228, 234, 324/236, 262, 158 D, 158 R, 158 F

[56] References Cited

U.S. PATENT DOCUMENTS

| | | | |
|---|---|---|---|
| 2,640,190 | 5/1953 | Rines | 73/628 |
| 3,067,387 | 12/1962 | Anderson et al. | 324/158 D |
| 3,312,893 | 4/1967 | Currin et al. | 324/158 D |
| 3,890,564 | 6/1975 | Watanabe et al. | 324/225 |

FOREIGN PATENT DOCUMENTS 197709 8/1977 U.S.S.R. .............................. 324/236

OTHER PUBLICATIONS

Botsco, "Eddy-Sonic Test Method", 2/1968, Materials Evaluation, pp. 21-26.
Poponiak et al., "Detecting Conductivity Type in Semiconductor Analysis", 6/1971, IBM Tech. Disc. Bull., vol. 14, No. 1, p. 100.

Primary Examiner—Gerard R. Strecker
Assistant Examiner—Walter E. Snow
Attorney, Agent, or Firm—Thomas Schneck

[57] ABSTRACT

An instrument for computing resistivity based upon measurements of thickness and conductance. A conductance transducer is a solenoid in an annular ferrite cup connected to a tank circuit for an eddy current measurement of conductance. Within the center of the annular ferrite cup concentric acoustic wave sending and receiving channels are disposed for making an acoustic pressure wave measurement which is used for a thickness measurement using two gauge heads, spaced on opposite sides of an article to be measured. Each gauge head contains identical conductance and thickness transducers. The thickness measurement is divided by the conductance measurement to derive resistivity.

29 Claims, 26 Drawing Figures

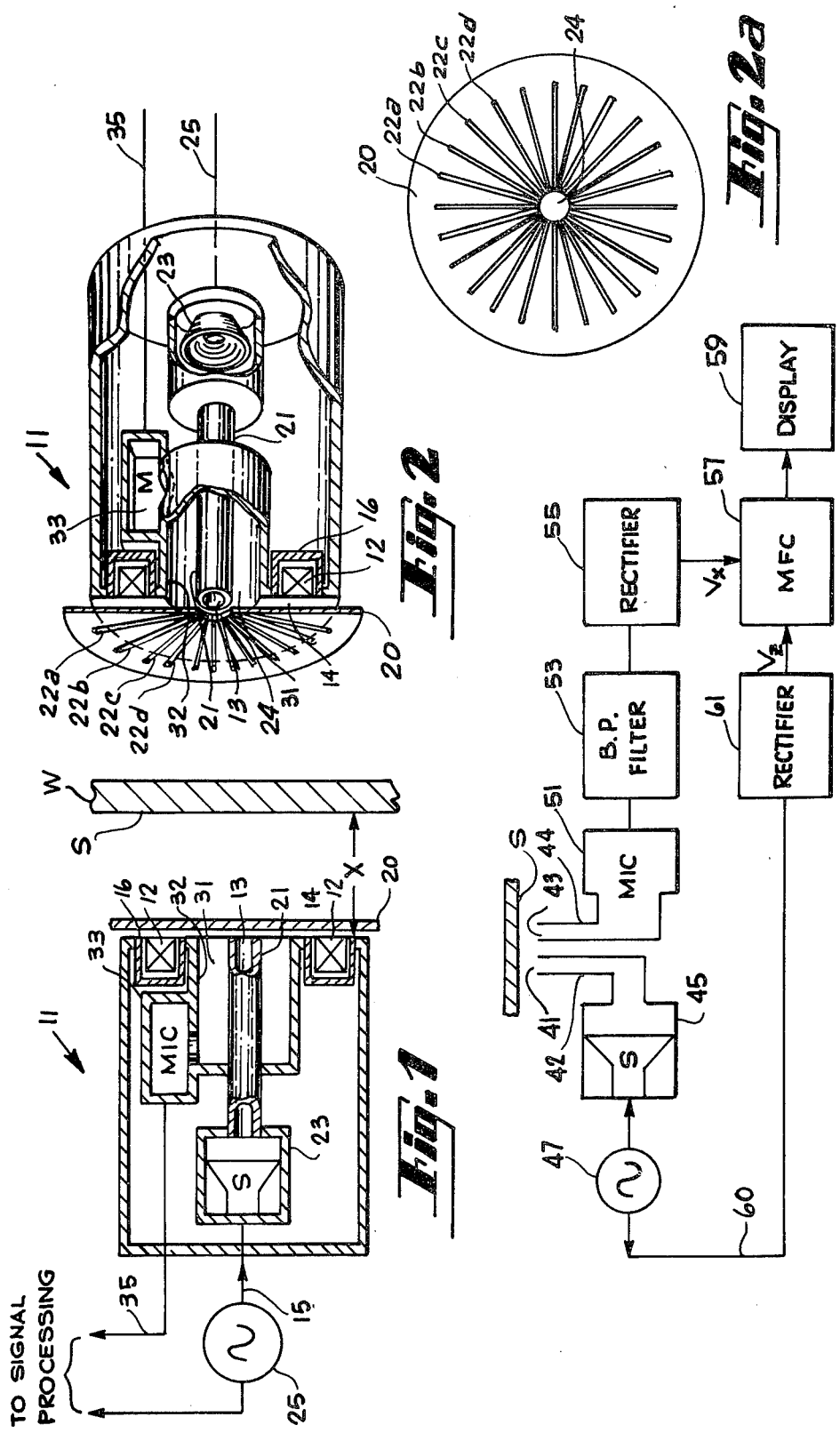

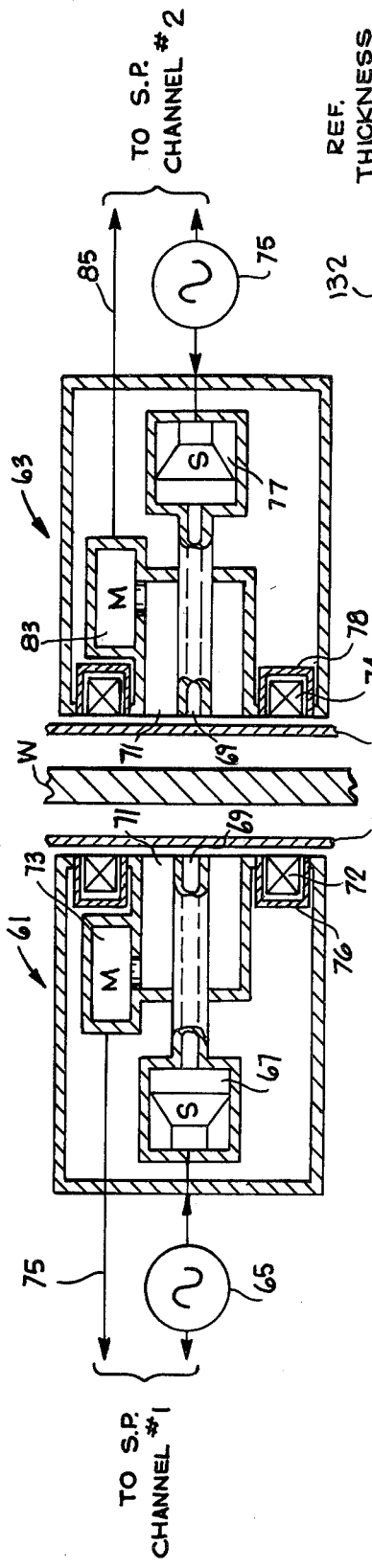
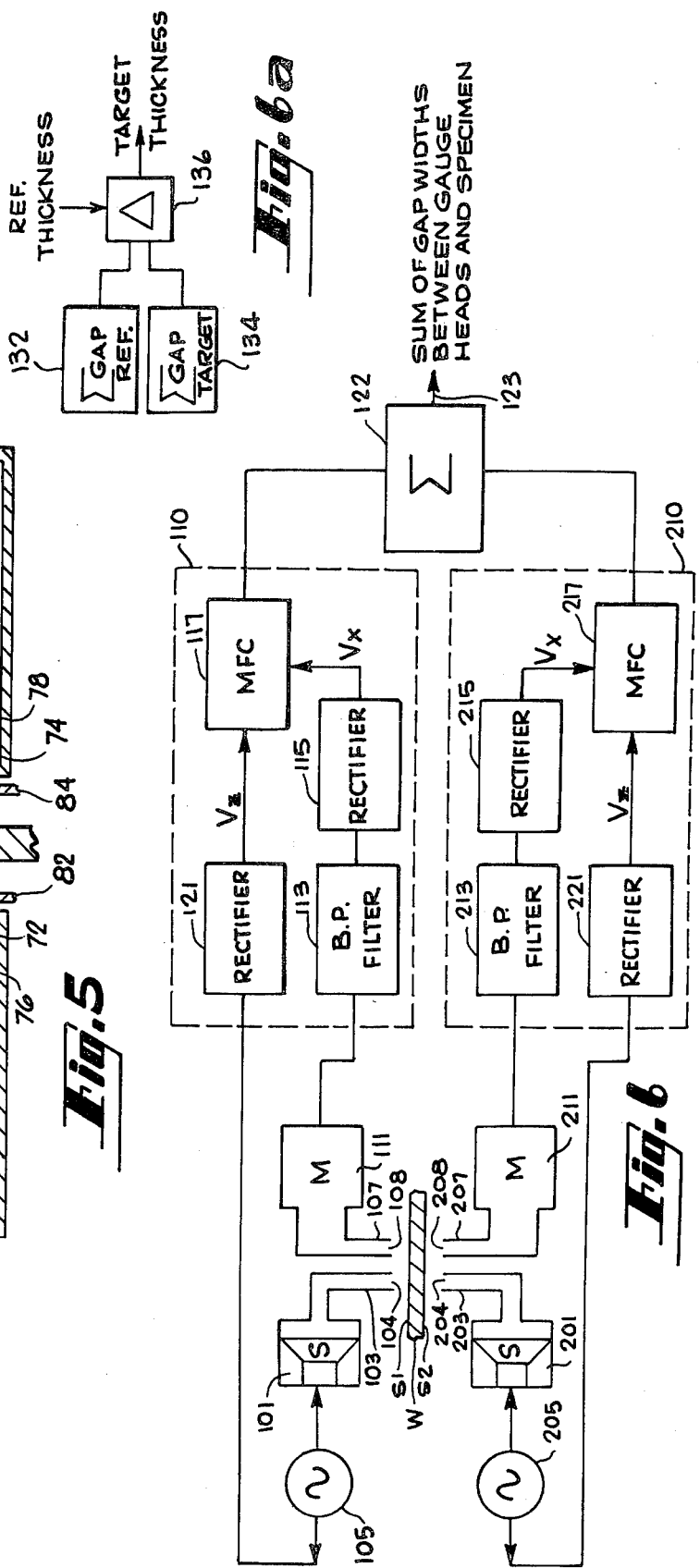

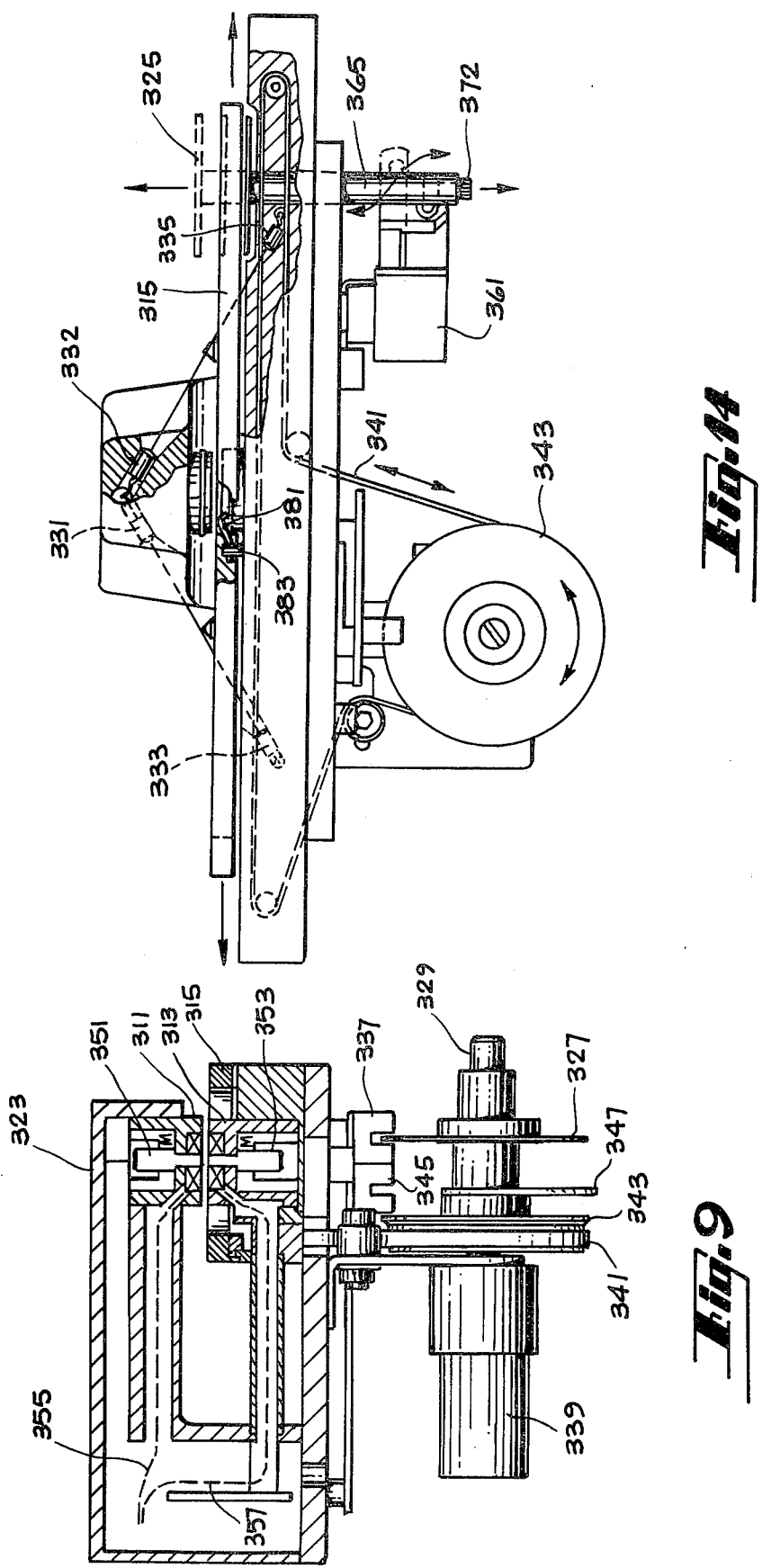

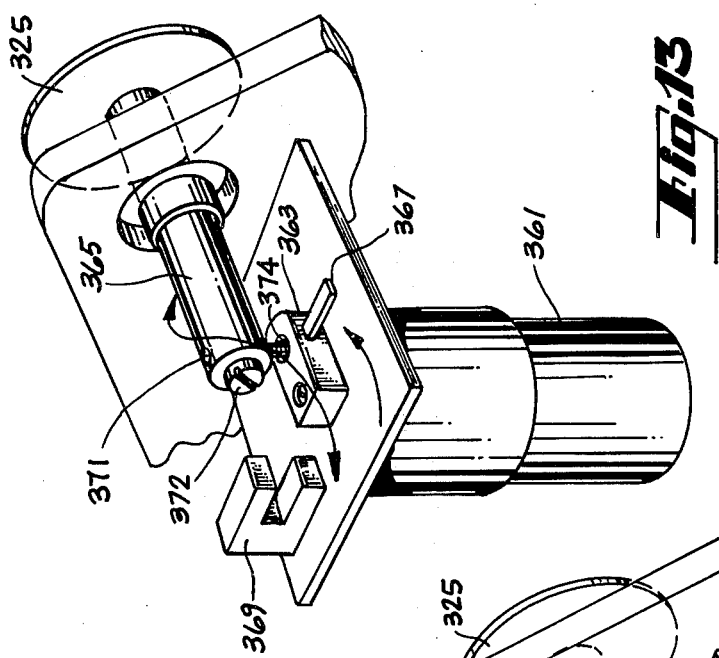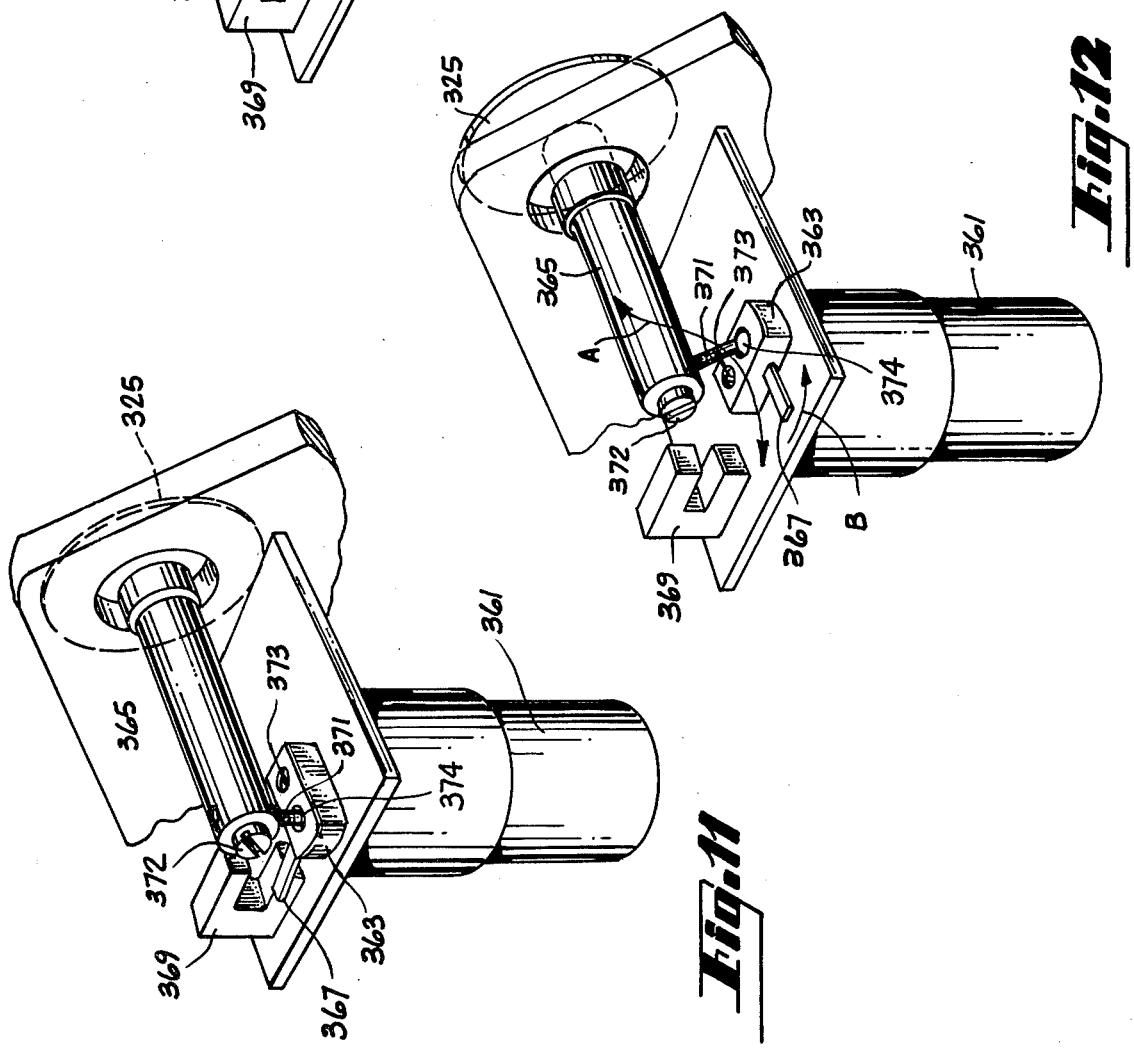

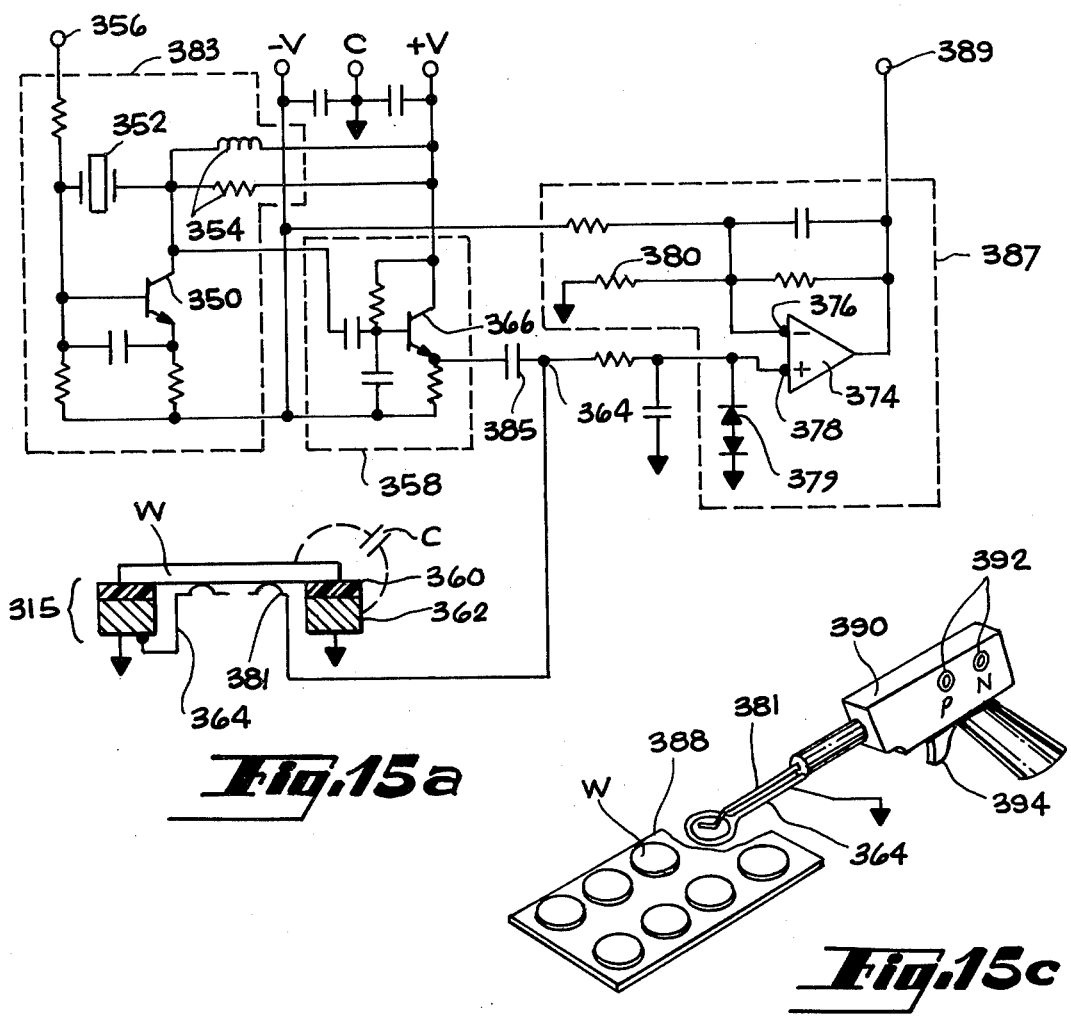
Fig.15a
Fig.15c
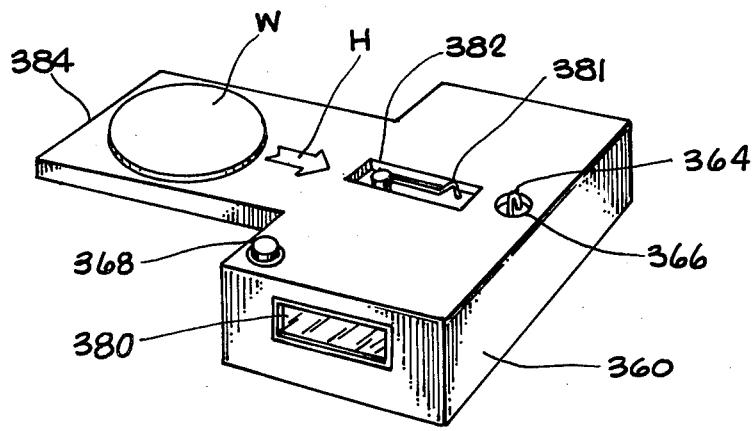
Fig.15b

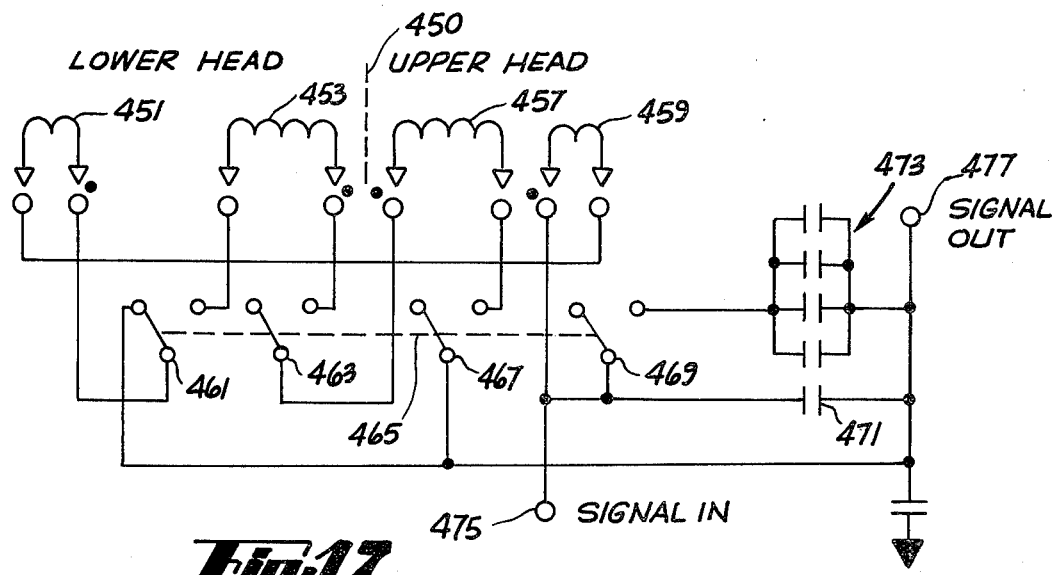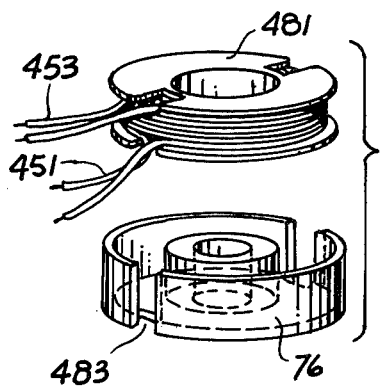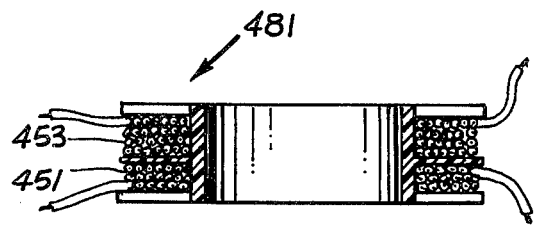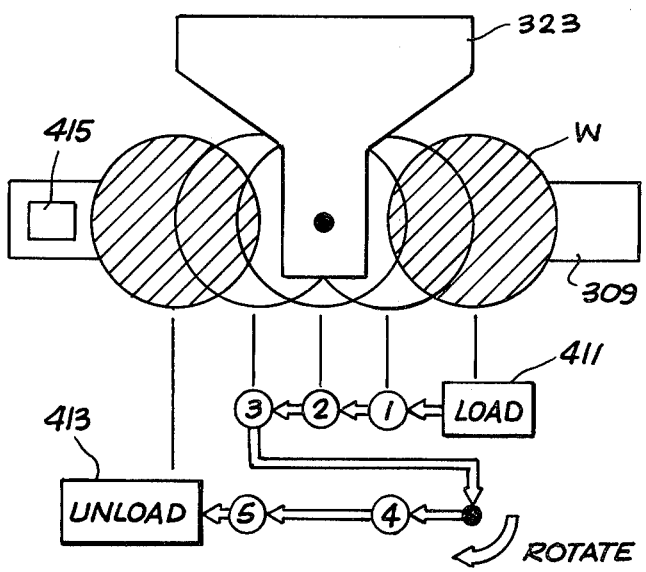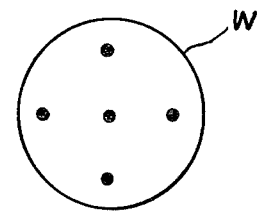

NON-CONTACTING RESISTIVITY INSTRUMENT WITH STRUCTURALLY RELATED CONDUCTANCE AND DISTANCE MEASURING TRANSDUCERS

CROSS REFERENCE TO RELATED APPLICATIONS

This is a continuation-in-part of application Ser. No. 903,493 entitled Gauge for Measuring Distance to Planar Surfaces and Thicknesses of Planar Members, filed May 8, 1978, now Pat. No. 4,175,441, and a continuation-in-part of application Ser. No. 941,233 entitled Improved Resistivity Gauge, filed Sept. 11, 1978, the latter now abandoned.

BACKGROUND OF THE INVENTION a. Field of the Invention

The invention relates to a resistivity measuring instrument and more particularly to a compact eddy current resistivity measuring instrument with gauge heads equipped with sensors for conductance and thickness measurements of test articles of unknown conductance and thickness.

b. Prior Art

In a co-pending patent application, Ser. No. 903,493, an apparatus is disclosed for measuring distance between a gauge head orifice and the front planar surface of an object by sensing acoustic pressure near the gauge head orifice. The acoustic pressure is initially generated by an audio oscillator activating a speaker which emits acoustic waves through a front orifice. Acoustic pressure is sensed through a second orifice, proximate to the first, and the pressure is converted to an eletrical signal which is processed to yield a distance signal. Two similar distance gauges spaced apart on opposite sides of a planar member at a known distance are used to compute the thickness of the planar member. While thickness measurements have application in many fields, one particular field of interest is in the measurement of resistivity of sheet materials in which eddy currents may be induced.

In an article entitled "Contactless Measurement of Semiconductor Conductivity by Radio Frequency-Free-Carrier Power Absorption" by G. L. Miller, D. A. H. Robinson and J. D. Wiley of Bell Laboratories, reported in Review of Scientific Instruments, vol. 47, No. 7, July, 1976, p. 799–805, a conductance gauge is disclosed in which a pair of ferrite cores are spaced on opposite sides of a sheet material, a semiconductor slice, for inducing eddy currents therein so that conductance can be determined. The ferrite cores are solenoids which are axially aligned and which cooperate with each other to form an axial magnetic field. The two solenoids are mutually connected through a capacitor forming a tank circuit which is resonant at a radio frequency. An oscillator is energized by a d.c. current which maintains a constant voltage across the resonant circuit. To measure conductance the d.c. current necessary to maintain the axial magnetic field is first read without any magnetically susceptible material in the magnetic field. Then the current is read with a test article in the field. The test article in the field damps the resonance of the circuit, causing additional Q loading. The authors of the above mentioned article have found that the additional power absorbed by the sheet material is accurately proportional to the material conductance.

The gauge described by Miller, et al. measures only conductance and in many applications it is important to know resistivity instead. Resistivity may be obtained by dividing thickness by the conductance of the test article. In the prior art, thickness was measured by air gauges or by other means which require a separate measurement, using a separate instrument.

One of the problems recognized by Miller, et al. is that at high radio frequencies at which conductivity measurements are made, there is a certain amount of electrostatic coupling to the sheet material. Miller, et al. recommend cementing a disc of conductive paper across the ferrite core as a solution to the problem of electrostatic coupling or capacitance which tends to change the character of the tank circuit by additional Q loading. The problem with conductive paper is that if it is too conductive the Q of the tank circuit significantly drops. If the paper is not conductive enough, it does not shield against electrostatic loading.

SUMMARY OF THE INVENTION

An object of the invention was to devise a measuring device for resistivity measurement of a generally flat test article, such as a semiconductor wafer, which combines a conductance sensor with a sensor for thickness measurement so that resistivity may be measured with a single instrument.

Another object was to devise a capacitive shield for a solenoid of the type which uses eddy currents for induction of a magnetic field in a test article for blocking capacitive coupling between the solenoid and the test article in conductivity measurements.

The above objects have been achieved in a resistivity instrument for magnetically susceptible, non-vibrating, generally flat test article, such as a semiconductor wafer wherein first and second gauge heads are mutually spaced a known distance on opposite sides of the test article whose resistivity is to be measured. Each gauge head has acoustic pressure means, including a speaker and a microphone disposed within the gauge head facing the test article and in acoustic pressure communication therewith. The speaker modulates ambient pressure toward a surface of the test article and establishes acoustic pressure in the gap between the speaker acoustic wave output and the surface of the article. The microphone detects acoustic wave pressure and produces a first electrical signal representing the amplitude of the detected acoustic wave modulation in the gap which is proportional to the gap distance. The gap distance on each side of the test article may be subtracted from the gap distance on each side of a reference specimen, plus the known specimen thickness to compute the thickness of the test article.

Solenoid means generating an axial magnetic field are also disposed in each gauge head surrounding the acoustic pressure means, such that the axial magnetic field is perpendicular to the plane of the test article. The magnetic field is sufficiently strong for inducing eddy currents in the article and producing an electrical signal representative of the conductance of the test article. By disposing the solenoid means about the acoustic pressure means a compact transducer structure is achieved for deriving conductance and thickness signals.

Electrical divider means are provided for dividing the thickness signal by the conductance, yielding a signal representative of the resistivity of the test article.

To block unwanted capacitive coupling between each gauge head and a surface of the test article, a capacitance shield is interposed between each solenoid and the surface of the test article. The capacitance shield is a grounded conductive planar member disposed generally perpendicular to the axial magnetic field of each solenoid. The capacitance shield has a plurality of radial slits therein extending outwardly from the axis of the axial magnetic field for preventing the magnetic induction of eddy currents therein but allowing capacitive currents to be shunted to ground thereby providing capacitive shielding for the test article. In the absence of such a shield, unwanted capacitance would drop the Q of the resident circuit formed by the solenoids in each gauge head in relation to the test article.

BRIEF DESCRIPTION OF THE DRAWINGS

FIG. 1 is a plan view of a resistivity gauge head of the present invention positioned for measuring resistivity of a test article.

FIG. 2 is a side cutaway view of the gauge head shown in FIG. 1, but reversed, left to right in orientation.

FIG. 2a is a frontal view of a capacitance shield to be interposed between the gauge head of FIG. 2 and test article whose resistivity is to be measured.

FIG. 4 is an electrical plan for a distance measurement utilizing the apparatus of FIG. 1.

FIG. 5 is a plan view of a resistivity gauge utilizing a pair of spaced apart gauge heads of the present invention.

FIG. 6 is an electrical plan for a head gap measurement in the apparatus of FIG. 5, illustrating signal processing means for gap width.

FIG. 6a is a logic plan for computing test article thickness from gap widths of a specimen object and a target test article.

FIG. 9 is a partially cutaway side elevation of the appartus of FIG. 8.

FIGS. 11, 12 and 13 illustrate a mechanism for rotating test articles on the carriage assembly shown in FIG. 8.

FIG. 14 is a partially cutaway front elevation of the apparatus of FIG. 8.

FIG. 15a is a more detailed electrical schematic of the wafer type sensor of FIG. 15.

FIG. 15b is a perspective view of an alternate housing for the circuit of FIG. 15a.

FIG. 15c is another alternate housing for the circuit shown in FIG. 15a.

FIG. 17 is an electrical schematic of a coil switching network used for resistivity measurements of test articles with differing conductivity.

FIG. 18 is an exploded perspective view of a ferrite core for holding a bobbin on which two coils of FIG. 17 are wound.

FIG. 19 is a side sectional view of the core of FIG. 18 housing the bobbin of that figure.

FIG. 20 shows an operating plan for a sequence of measurements using the apparatus of the present invention.

FIG. 21 shows a series of test points on a specimen wafer using the operating plan of FIG. 20.

DESCRIPTION OF THE PREFERRED EMBODIMENT

Figure 3:
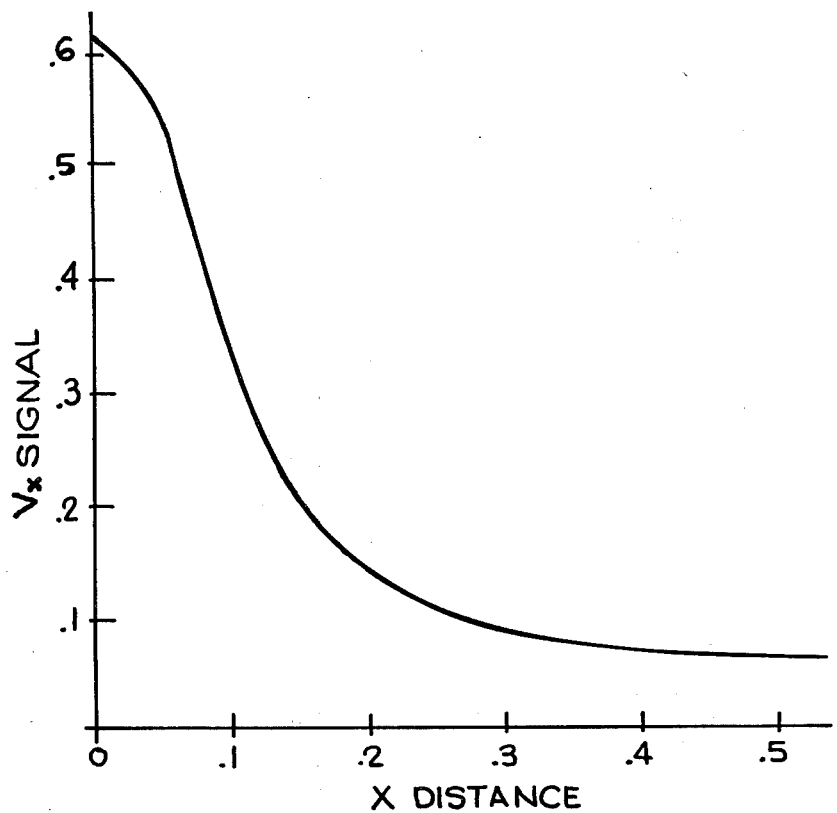
FIG. 3 is a plot of a pressure dependent signal versus distance between a pressure source and a planar surface of a test article.

With reference to FIG. 1, a plan view of a gauge head 11 for a resistivity gauge of the present invention is shown. The head may be cylindrical or prism shaped, having two orifices 13, 31 on one end and electrical leads 15, 35 emerging on the other end, although electrical leads may emerge from any side of the land. Orifices 13, 31 are used for a thickness measurement of the gauge head by generating acoustic pressure.

The gauge head also has the solenoidal coil 12 mounted in a magnetically permeable cup, a ferrite core 16, such that the solenoid 12 may generate an axial magnetic field with the field axis generally corresponding to the center of orifice 13, although this need not be the case. Solenoid 12 surrounds the orifices 13, 31. Electrical wires for energizing the solenoid 12 are not shown. Preferably, the ferrite core has a U-shaped cross section with the open end facing a specimen. In practice, the solenoid has only a few turns of wire, but these are sufficient to generate an axial magnetic field.

In the preferred embodiment, the gauge head is cylindrical with a length of approximately 30 mm. and a diameter of approximately 22 mm. These dimensions are exemplary. The dimensions selected by a user should be large enough to accommodate the components of FIG. 1 described below, although some of the components could be located outside of the gauge head if an especially small gauge head is required.

The axial magnetic field generated by solenoid 12 is intended to induce eddy currents in flat test article W, having the frontal surface S. The eddy currents are established by magnetic induction, so that test article W must be at least partially magnetically susceptible. As described hereinafter, the conductance of the article W may be measured by an eddy current described herein and by dividing the thickness signal by the conductance of the test article W resistivity of the test article may be computed. The gauge head of the present invention contains sensors for measuring both conductance and thickness. Thickness is measured by means of establishing acoustic pressure between the gauge head 11 and the frontal surface S of article W by means of a speaker 23 which generates acoustic pressure and a microphone 33 which detects the amplitude of acoustic pressure in the gap between the face 14 of gauge head 11 and the frontal surface S of the test article W.

The first orifice 13 is an acoustic wave modulation output located at the end of a conduit or tube 21 which extends from the orifice 13 to a miniature speaker 23. Miniature speaker 23 is a commercially available device measuring approximately 10 mm on a side and approximately 4 mm. thick. The speaker is commercially known as a receiver, model BB-1511 available from Knowles Electronics, Inc., Franklin Park, Ill. Speaker 23 is electrically driven by a low power solid state audio oscillator 25 which is connected to speaker 23 by means of a wire pair 15. The frequency of audio oscillator 25 is not critical, but a frequency below 20,000 hertz is preferred. The exact frequency selected should be one which yields an optimum signal to noise ratio for the entire system, taking into account the sensitivity of an acoustic pickup transducer described below. Orifice 13 is parallel to, but spaced from, a planar surface, S, of an object, W, such as a substrate, a semiconductor wafer or other non-vibrating object. Typically, the substrate may be supported by a carriage, as described below.

The gauge head 11 preferably has a face 14 which is a panel or wall, having the orifices 13, 31 defined therein. In FIGS. 1 and 2 face 14 is shown to be annular with orifices 13, 31 defined coaxially in the center thereof. Exemplary dimensions for gauge dimensions are as follows. Head 11 is made cylindrical with a face diameter of 2.2 cm, a first orifice 13 diameter of 1.6 mm surrounded by conduit 21 having a diameter of 2.1 mm. Second orifice 31 coaxially surrounds first orifice 13 and has a diameter of 3.2 mm. These dimensions may be varied by those skilled in the art and are not critical. The diameter of the face, if annular, should be at least two or three times the gap distance to be measured, although for various applications, the shape and size of the head and face could vary considerbly.

While the face 14 is preferable in providing a structure which holds the first and second orifices, face 14 is not essential if the orifices are independently supported, as they are shown in FIG. 4 wherein the orifices 41, 43 are defined at the ends of tubes 42, 44 respectively. The benefit of face 14 is that it increases sensitivity of the apparatus, i.e., the ability of the apparatus to pick up weak signals.

Returning to FIG. 1, second orifice 31 is an acoustic wave input which communicates with the sensitive portion of a microphone 33 through a conduit or tube 32. Microphone 33 is approximately the same size as speaker 23. Such a microminiature microphone is also available from the same supplier mentioned above and has a commercial designation of BA 1502. A pair of wires 35 emerging from microphone 33 is connected to signal processing means described below with reference to FIG. 4.

In operation, the audio oscillator 25 generates an electrical signal having a frequency below 20 KHz and preferably about seven or eight hundred hertz. Frequency is not critical but frequency and amplitude of oscillations must remain constant during a gap measurement. The eletrical signal is transformed into acoustic waves by speaker 23. Acoustic energy is transmitted down conduit 21 to orifice 13. Acoustic pressure is built up between orifice 13 and surface S which appears as a wall or barrier to the gauge head. It is necessary that the surface S be large enough so that some acoustic pressure may be built up. For small surfaces the gauge head must be closer to the surface than for very large surfaces, where the gauge may be further away. In either instance, it is necessary for the gauge to be able to sense pressure between the gauge head and the surface S.

Pressure modulation by acoustic waves in the gap between the gauge head and the surface S is detected through the second orifice 31 which communicates with microphone 33. The amplitude of acoustic waves between the gauge head and surface S is detected by the microphone 33. In contradistinction to the prior art, the present apparatus is not measuring phase changes of waves, or the time of arrival of pulse echos. Rather, it is measuring acoustic pressure between the gauge head and the surface S, of a gaseous sonic medium, such as air in the gap. The apparatus of the present invention will not operate in the absence of a sonic medium, as in a vacuum. There are no restrictions on the sonic medium, except that its properties remain generally constant during the brief measurement interval.

It should be noted that the preferred acoustic frequency of seven or eight hundred hertz has an audio wavelength of a few meters. This is long compared to a typical spacing from a gauge head to a test object needed to build up acoustic pressure. Such a typical spacing might be a few millimeters. The acoustic waves need not have such a long wavelength inasmuch as shorter waves will also work.

In the appartus of the present invention, the speaker 23 modulates ambient pressure between the orifices and the surface S with acoustic waves. This modulation may be thought of as an a.c. pressure component being impressed upon a d.c. pressure component, where the speaker modulation is the a.c. pressure component and ambient pressure is the d.c. pressure component. The speaker does not add any ambient pressure but only modulates ambient pressure with acoustic waves. This modulation is detected by a microphone and converted to electrical wave oscillations which are subsequently filtered and rectified to a d.c. voltage, analogous to rectification of radio frequency waves in a simple radio. This d.c. voltage is proportional to the a.c. pressure component in the gap between surface S and the orifices. If the surface S is further away, the amplitude of acoustic waves detected will be smaller than when the surface S is closer to the gauge head. A wire 35 carries away signals from the microphone 33 for signal processing. While a microphone is a preferred acoustic wave detector, other types of transducers which sense acoustic wave amplitude could be used.

With regard to operation of the solenoid 12, the electrical circuits for generating the axial magnetic field through the solenoid, as well as the circuits for detecting conductivity are described in the aforementioned article by G. L. Miller, et al. in Review of Scientific Instruments, vol. 47, No. 7, July, 1976, p. 799–805, incorporated by reference herein. Briefly, the article describes how a magnetic field may be established by means of a solenoid which is in parallel with a capacitor. A radio frequency current generator is placed across the LC circuit formed by the coil and capacitor which are connected in parallel. The voltage across the LC pair is maintained constant and the amount of d.c. current into the circuit is measured both without the sheet material present and with the sheet material present. The LC circuit is a tank circuit which is resonant at a radio frequency. The power absorbed by the sheet material is linearly proportional to its conductance and since voltage across the circuit is maintained at a constant level, the current into the circuit is linearly proportional to conductance. The constant of proportionality can be determined empirically so that a measure of power absorbed by the sheet material may be read as a value of conductance.

The above mentioned article by Miller, et al. mentions that some electrostatic coupling exists between surface S of test article W and the solenoid 12. To limit this electrostatic coupling which has the effect of damping the Q loading of the LC resonant circuit, a capacitance shield 20 is interposed between solenoid 12 and test article W. Preferably, the capacitance shield is adhered to face 14 of the gauge head. Capacitance shield 20 has a novel construction which is described below with reference to FIG. 2a.

FIG. 2 shows a side view of the gauge head of FIG. 1. The head 11 may be seen to be cylindrical with the first orifice 13 located coaxially within the annular second orifice 31. The first orifice need not be within the second orifice, but may be in a side-by-side relationship or other adjacent location. It is necessary that the second orifice be in a position to accurately sense pressure modulation generated by sound waves emitted from the first orifice.

The coaxial joint geometry of FIG. 2 is preferred because the annular second orifice 31 provides a large aperture for receiving reflected energy while limiting the size of the overall gauge head. Tube 32 which defines second orifice 31 may be part of the gauge head body, such as an inside diameter or may be a separate tube mounted in the gauge head. It is desirable to keep the conduit 21 short in order to avoid any unwanted acoustic impedances. Similarly, the microphone 33 communicates directly with the orifice 31 through tube 32 in order to limit the loss of acoustical signal between the orifice and the microphone.

FIG. 2 shows the annular ferrite core 16 having a U-shaped cross section within which the solenoid 12 is disposed. The core tends to direct the field from solenoid 12 in a direction away from face 14 of gauge head 11 toward the surface of an article being measured. The capacitance shield 20 may be seen to be mounted in front of face 14 and in particular covering the ferrite core 16. Capacitance shield 20 is electrically grounded and made of a conductive planar member which is disposed generally perpendicular to the axial magnetic field generated by the solenoid 20. The capacitance shield has a plurality of radial slits 22a, 22b, 22c, 22d, etc. These radial slits extend from a central aperture 24 in the center of the capacitance shield 20 which is designed to allow acoustic pressure communication through orifices 13, 31 for unimpeded acoustic pressure measurements. The size of aperture 24 corresponds with the diameter of the orifice 31.

With reference to FIG. 2a, a frontal view of the capacitance shield 20 shows a plurality of radial slits extending from central aperture 24 and extending outwardly. The slits are equally spaced and are preferably very thin to prevent capacitive leakage. The capacitance shield is preferably less than 10 mils thick and is made of an aluminum layer of polyester film.

In order to make the slits 22a, 22b, 22c, 22d, etc., photoresist is placed on the aluminum side of the shield in a uniform layer. The desired slit pattern is placed on the photoresist as a latent image which is then developed. The metal having the slit pattern is then etched away either chemically or by means of plasma etching. Using this technique, slits which are only a few mils wide may be made. After etching, the remaining photoresist is washed away and hoop is used to mount the shield to the face of the gauge head and electrically ground it to the support structure. The advantage of small slits is to minimize undesired capacitance. In the center of the slit pattern, a central aperture 24 is cut so that acoustic pressure measurements may still be made through the center of the shield. The size of aperture 24 should be large enough so that the tubes through which acoustic pressure is emitted and received can both communicate outwardly with the surface to be measured through the aperture 24.

FIG. 3 is a graph showing the relationship between the amplitude of the d.c. level signal, $V_x$, and the distance, X, between the orifices 13, 31 of FIG. 1 and the surface S. It will be seen that the acoustic signal is maximum at zero distance and diminishes as distance increases. This is a generalized plot for the relationship between a surface S and a gauge head 11, as shown in FIG. 1. The curve which is shown in FIG. 3 has the relationship $V_x = A/(B + X^n)$ where A and B are empirically determined constants dependent on construction geometry, such as size and position of orifices. This is a relationship in which X is determined by the signal processing means of the present invention. One of the advantages of the present invention is the ability to operate anywhere on the curve and beyond the right hand edge, due to mathematical processing of the quantity $V_x$.

With reference to FIG. 4, a surface S is shown to be facing a first orifice 41 which is adjacent to a second orifice 43. Note that in this example, the orifices are not coaxial, but are adjacent to each other. First orifice 41 is connected to speaker 45 through self-supporting or cantilevered tube 42 which is driven by the audio oscillator 47. Acoustic pressure between orifice 41 and surface S is detected by microphone 51 through the second orifice 43 which is connected thereto through self-supporting or cantilevered tube 44. An electrical signal is generated by microphone 51 having an amplitude which is proportional to the amplitude of the detected acoustic pressure from acoustic waves in orifice 43. The detected signal is sharply filtered by the band pass filter 53. Band pass filter 53 is strongly peaked at the frequency of the audio oscillator 47. The filtered signal is transmitted to a full-wave rectifier 55 which has smoothing filters at its output such that the rectified signal is smoothed to a d.c. level which is fed to a multifunction converter (MFC) 57.

As mentioned above, our requirement is to solve the equation $$V_x = \frac{A}{B + X^n} \quad (1)$$

Multifunction converter 57 solves the equation $$E_o = V_y \left(\frac{V_z}{V_x}\right)^m \quad (2)$$

Multifunction converter 57 is preferably a commercial device known as an LH0094 Multifunction converter manufactured by National Semiconductor Corporation of Santa Clara, California, or similar analog multiplying device.

Although not required to calculate the distance between the surface and the gauge head, we have found it preferable to take the output of the audio oscillator 47 through line 60 and connect it to a second rectifier 61, identical to rectifier 55. This enables multifunction converter 57 to execute equation (2) where the scaling term $V_y$ is a reference or calibration voltage, the term $V_z$ is a reference voltage obtained from rectifier 61 and the term $V_x$ is a voltage signal derived from rectifier 55. The purpose for taking another signal from audio oscillator 47 through rectifier 61 is to detect any fluctuations in the oscillator power supply which may cause systematic variations in the signal fed to multiplier 57. By using the ratio $V_z/V_x$, fluctuations will cancel, leaving only the magnitude of the pressure signal in the equation, together with a multiplying constant, $V_y$, as well as the empirically determined exponent "m". The multiplying constant $V_y$ adjusts the slope of the desired output signal for driving the display 59.

The exponent "m" of equation (2) must be between 0.1 and 10 according to the manufacturer of the multi-function converter. It has been determined that an optimum value of "m" is 1.1 for the apparatus of FIG. 1 by curve fitting measured values of $V_x$ to values of $V_x$ expressed by equation (1).

In FIG. 4, the reference signal $V_z$ was derived directly from audio oscillator 47 as an electrical signal. There are other ways in which a reference signal could be generated. For example, instead of deriving $V_z$ directly as an electrical signal, it may be derived indirectly in the following manner. The enclosure for speaker 45 may be tapped with a tube or conduit 46 leading to another microphone 48 which directly senses the output of speaker 45 and converts the detected acoustic wave to an electrical signal which is then fed to rectifier 61. Alternatively, the output of speaker 45 could be sampled by a microphone 50 having an input adjacent to microphone 50. In these situations, rectifier 61 would not receive an electrical input along the line 60 from audio oscillator 47, but from microphone 48 or 50.

A variation of an apparatus for deriving the reference signal, $V_z$, is to sample the output of speaker 45 near the orifice 41 of tube 42, but at a known fixed distance from surface S. The microphone would convert detected acoustic signals into electrical signals which are fed to rectifier 61. In the latter two instances where microphones are used to detect acoustic waves from speaker 45, band pass filtering prior to rectification is preferable, using sharp filtering at the frequency of audio oscillator 47.

FIG. 5 shows a pair of gauge heads 61, 63 spaced apart on opposite sides of a thin flat article W. Each of the gauge heads 61, 63 is similar to the gauge head described with reference to FIG. 1, except that they should each have speakers driven by audio oscillators at different frequencies. The total distance between the gauge heads is known. Since each gauge head can establish the distance between the head and the surface of article W facing the head the thickness of member W may be computed by a simple subtractive process. Each gauge is connected to a separate signal processing channel so that the two head-to-surface measurements may independently be made. Audio oscillator 65 of the first gauge head drives speaker 67 which emits acoustic waves through the first orifice 69. Acoustic pressure between the gauge head and the second orifice 71 is detected by microphone 73 which puts out an electrical signal having an amplitude proportional to the acoustic pressure in the second orifice 71. This electrical signal is transmitted along wire 75 to signal processing channel number 1.

Similarly, the gauge head 63 has an audio oscillator 75 which drives speaker 77 at a different frequency from speaker 67. Speaker 77 puts out acoustic waves through the first orifice 79 which faces the back surface of article W. Acoustic pressure between the surface of member W and the gauge head is sensed through the second aperture 81 which communicates with microphone 83. Microphone 83 converts acoustic pressure amplitude into electrical signals whose amplitude is proportional to pressure which signals are taken along line 85 to the second signal processing channel.

Each of the gauge heads 61, 63 have a respective solenoid 72, 74 therein, each mounted in a respective annular ferrite cup 76, 78. The solenoids 72, 74 are mounted in the head 61, 63 so that they are in axial alignment and are constructed to be approximately the same size. The electrical connection of the two solenoids is such that a single magnetic field is generated by the two solenoids and is an axial magnetic field passing through the solenoids, as well as through the article W whose conductivity is measured by eddy currents developed therein. The two solenoids 72, 74 are connected in parallel with a capacitor, thereby forming a tank circuit having high Q in the absence of sheet material.

When the test article W is interposed between the two heads 61, 63 there is some damping of the Q of the tank circuit and the additional current into the circuit which is necessary to maintain a constant voltage is proportional to the conductance of the sheet material.

As previously mentioned, capacitance shields 82, 84 constructed in accord with FIG. 2a are adhered to the face of each of the gauge heads 61, 63 to limit unwanted electrostatic coupling between the gauge heads and the article to be measured. Each of the capacitance shields 82, 84 are electrically connected to ground. In measuring conductivity, the thickness measurement which is made by the acoustic pressure means within the gauge heads is not absolutely necessary, merely very convenient to have both the thickness transducers and the conductivity transducers in the same gauge heads. However, if the thickness transducers are not in the same gauge head and a prior art method of thickness measurement is used, the capacitance shields of the present invention would still be used to shield the solenoids from undesired capacitive coupling to the sheet material to be measured. In this regard, the capacitance shields of the present invention could be used with prior art solenoids in eddy current measurements to limit capacitive coupling between the solenoids and the objects being measured or tested.

The circuit for measuring conductivity from two opposed solenods, as shown in FIG. 5 is described in the article by Miller, et al., mentioned previously. Once thickness is known, that value may be divided by conductance in order to obtain resistivity. The circuit for obtaining a thickness measurement from the opposed thickness transducers is shown in FIG. 6.

With reference to FIG. 6, an electrical plan for the connection of two gauge heads is shown. The gauge heads are similar to the two heads illustrated in FIG. 5 with the exception that a coaxial geometry is not used, although it could be used. In FIG. 6 a first speaker, disposed within an enclosure having a conduit 103 extending therefrom transmits acoustic pressure from the speaker enclosure through the conduit 103 to an orifice 104 facing the surface S1 of a test article W.

Adjacent to conduit 103 is conduit 107 which has a second orifice 108 adjacent to orifice 104. The second orifice 108 picks up the acoustic pressure between the first orifice and the surface S1 and transmits the pressure signal through conduit 107 to microphone 111. Microphone 111 produces an electrical signal whose amplitude is proportional to the amplitude of the acoustic pressure sensed in the second orifice 108 connected to microphone 111. The electrical signal is transmitted into a first signal processing channel indicated by the dashed line 110 which includes a sharp band pass filter 113 which is strongly peaked at the frequency of oscillator 105. The filtered signal is transmitted to rectifier 115 which rectifies and smooths the signal to a d.c. level and then transmits the signal to multiplier 117.

Audio oscillator 105, besides driving speaker 101 also provides an oscillator signal to rectifier 121 which is identical to rectifier 115. A rectifier 121 rectifies and smooths the signal received from audio oscillator 105 to a d.c. level and transmits the signal to multifunction converter 117. The multifunction converter 117 performs the same as multifunction converter 57 in FIG. 4 wherein the signal from rectifier 121 is treated as a reference voltage for canceling any variations in the signal received from rectifier 115 which are systematic, for example due to fluctuations in the power supply. The signal received from rectifier 121 is the numerator in the function handled by multifunction converter 117 while the signal received from rectifier 115 is the denominator. The entire expression is operated on by an exponent, n, whose value is determined empirically as previously described. The entire expression may be multiplied by a constant in order to achieve a desired level for transmission to the signal summing unit 122 which may be an operational amplifier.

A second gauge head, identical to the first gauge head is based on the opposite side of the test article W. Speaker 201 in an enclosure has a conduit 203 leading from the enclosure outwardly toward a surface S2 of article W. The end of conduit 203 terminates in a first orifice 204. The speaker 201 provides acoustic energy to the conduit 203 which is derived from the audio oscillator 205. Acoustic pressure which is built up between the orifice 204 and the surface S2 is detected by a second orifice 208 in the conduit 207 which is connected to microphone 211. Microphone 211 senses pressure amplitude near the first orifice 204 and puts out an electrical signal whose amplitude is proportional to the pressure amplitude near the first orifice 204. The pressure signal from microphone 211 is transmitted to band pass filter 213 which is strongly peaked at the frequency of audio oscillator 205. Note that the frequency of oscillator 205 should be sufficiently different from oscillator 105 that the respective band pass filter 113, 213 can easily separate the two signals if required to do so.

The filtered signal from filter 213 is transmitted to rectifier 215 which rectifies and smooths the electrical signal received therefrom. The smooth signal resembles a d.c. signal and is transmitted to multifunction converter 217. Multifunction converter 217 receives another electrical input from rectifier 221 which is in turn connected to receive a signal from oscillator 205. The signal from oscillator 205 is rectified and smoothed by rectifier 221 in the same way that rectifier 121 operates and the resultant signal is transmitted to the multifunction converter 217 to serve as the numerator of a fraction wherein the signal derived from rectifier 215 is the denominator. The fraction is raised to the n power where n is an exponent (near unity) determined empirically as previously described. The entire function is multiplied by a constant adjusting the amplitude of the entire signal for presentation to the summing amplifier 122. The summing amplifier 122 adds the outputs from the channels 110 and 210, thereby providing a proximity signal, indicated by arrow 123, which is equal to the sum of the distances from each gauge head where the orifices are mounted to a surface of article W facing the gauge head.

This proximity signal for each gap is summed and the combined signal representing the sum of the gaps is termed $V_{gap}$. In operating the instrument of the present invention the gauge head spacing, i.e., the total spacing between gauge head orifices, may change due to thermal effects. Since the thickness being measured is intended to be accurate to within a few microns these thermal effects can be significant. If the instrument is to be operated briefly, so that thermal effects are not significant, the thickness of a test object is easily computed in a difference amplifier, not shown, which subtracts $V_{gap}$ from a signal which may be provided representing the total distance between heads, $V_{spacing}$.

In the preferred embodiment it is contemplated that thermal effects will be significant. To take these effects into account a reference specimen having good insulative properties to prevent eddy currents therein such as a flat, stiff, ceramic wafer, is provided as a reference. The thickness of the reference specimen is preferably approximately the same as the target or test article, although this is not necessary. For semiconductor wafers an exemplary thickness for the reference specimen is 400 microns. To compute thickness of a test article, such as a semiconductor wafer, the proximity signals for the gaps between each gauge head and the front surface of a specimen and article are measured, first for the reference specimen of known thickness, then the target article of unknown thickness. This is shown diagrammatically in FIG. 6a. The $V_{gap}$ signal for a reference specimen is stored in a storage register 132 after the summing amplifier 122 in FIG. 6 derives this signal for the reference specimen of known thickness passing between the gauge heads. The analog output of summing amplifier 122 is converted to digital form in an analog-to-digital converter, not shown. Next, a target article of unknown thickness passes between the gauge heads and the $V_{gap}$ signal for the object is sent to register 134. Next, the outputs of the two registers are transmitted to an arithmetic unit 136 which also receives as an input signal the thickness of the reference specimen. This input is manually entered, as by thumb wheels. The $V_{gap}$ signal for the reference material is added to the signal representing the thickness of the reference specimen. From that total the arithmetic unit 136 subtracts the $V_{gap}$ signal for the target article yielding a signal for thickness of the target article. Thus, the instrument automatically compensates for thermal effects which would otherwise cause drift in the measurements. In the description below, the test article W is referred to as a semiconductor wafer. While the test article may be such a wafer, it need not be one. For example, it may be a thin film, a substrate material, or the like.

Note that in the configuration of FIG. 6 the conduit for the speaker and microphone of a gauge head are not concentric, but are mounted adjacent to each other. The conduits need not be parallel to each other but it is preferable that the orifice of a speaker, for example orifice 104, be adjacent to the second orifice of a microphone, 108 so that the microphone accurately senses changes in pressure between the surface and the first orifice 104 emitting acoustic waves.

Figure 7:
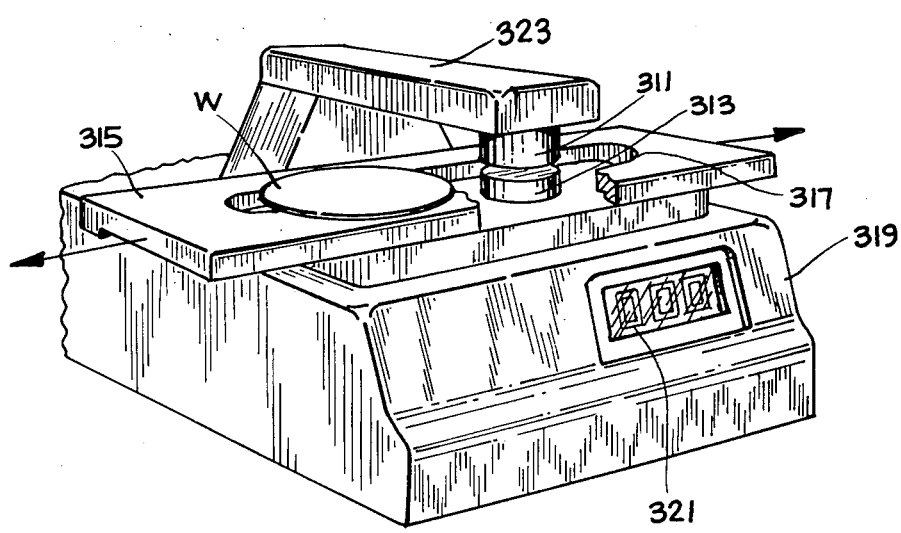
FIG. 7 is a perspective view of the mechanical mounting of the gauge heads of FIG. 5.

FIG. 7 illustrates the mechanical construction for a gauge of the type described with reference to FIG. 6. A pair of gauge heads 311, 313 are disposed opposite and facing each other with a gap therebetween. Each gauge has a face defining first and second orifices as previously described. The gap is wide enough to allow the test article, such as a silicon wafer, W, to pass therebetween. Wafer W is carried by a reciprocating plate or carrier 315 whch is driven by a motor which allows various portions of the wafer W to remain stationary between the heads 311, 313 for a measurement to be performed. Carrier 315 has an oval cut out region defined by wall 317 so that the carrier does not interfere with the measurement being made.

In FIG. 7, the approximate gap separation of the heads 311, 313 is between 1.1 mm and 1.2 mm with head diameters of approximately 22 mm for measuring the thickness of a member which fits between the heads. The upper surface of carrier 315 is at an elevation a few tenths of a millimeter higher than the face of head 313 so that a test article placed on the surface of the carrier will be spaced between the two heads, although it need not be spaced midway therebetween. The circuits shown in FIG. 6 are mounted in a cabinet 319 having a display window 321. The shape of the cabinet and display are selected for aesthetic appeal and are not critical to the operation of the apparatus. Similarly, the cantilever arm 323 supporting head 311 is designed chiefly for convenience and other forms of support for head 311 may be selected.

Figure 8:
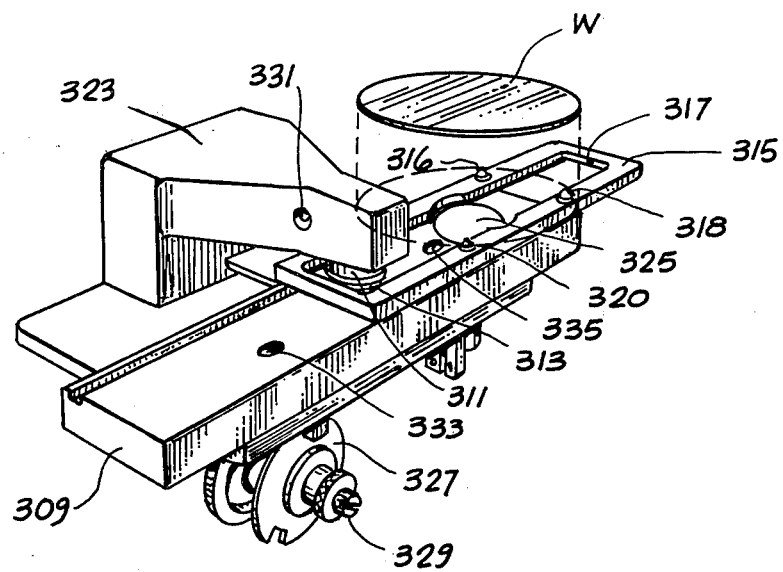
FIG. 8 is a perspective view of a detail of the carriage assembly and gauge heads of FIG. 5.

With reference to FIG. 8, a perspective view of a slightly modified cantilever arm 323 is shown which is functionally equivalent of the same member shown in FIG. 7. Carrier 315 has pins 316, 318, 320 for centering the wafer W in a desired location. Carrier 315 has an elongated cutout region 317 which provides clearance for a turntable 325 to be elevated within the carrier and come into contact with wafer W in order to rotate it, as described below. The elongated cutout region 317 has a length greater than an article to be measured, whereby carrier 315 encompasses the gauge heads at all times as the carrier moves back and forth. This is important because it enables the full diameter of a wafer, positioned on the carrier, to pass between the gauge heads. The upper surface of the carrier is slightly higher than the face of the lower gauge head, so that an article on the carrier passes midway between both gauge heads. The motion of carrier 315 is programmed by a film disk 327 which is mounted on a hub by means of a removable screw 329. Film disk 327 is opaque except for a pattern of radial transparent stripes which are read by a photodetector, as described below.

Photo diodes are mounted on each side of arm 323. For example, photo diode 331 is aimed angularly downward at photo detector 333 mounted within a hole in base member 309 which supports carrier 315. Another photo detector 335 is mounted in base member 309 on the opposite side of arm 323 to receive light from a photo diode, not shown, in arm 323. The two light beams serve to sense the position of carrier 315 as it carries wafer W back and forth between heads 311, 313.

With reference to FIG. 9, film disk 327 may be seen to be mounted so that at least a portion of the disk passes through the optical switch 337. Optical switch 337 has a photo diode on one side of the film disk and a photo detector on the other side for detecting transparent regions of film disk 327. Most of the film disk is opaque, except for the radial stripes previously described. A pattern of narrow and wide transparent stripes provides a code which controls operation of the apparatus. The strips are caused to rotate passed the optical switch 337 by means of a motor 339 which also drives the carrier 315 by means of a belt 341 mounted on a pulley 343.

As motor 339 provides motion for carrier 315 it also causes rotation of film disk 327. A narrow transparent stripe in the otherwise opaque film disk may be an instruction for the motor to stop, make a measurement, then continue. A wide transparent stripe may indicate that the motor is to stop, the apparatus to take a measurement and then reverse to repeat the process. The same stripe may be an instruction or command for specimen rotation in the horizontal plane, as described below.

One or more optical limit switches 345 are positioned adjacent to the first optical switch 337. An opaque member 347, which may be a metal arm or the like is adapted to pass through the optical switch 345. This limit switch signals the loading and unloading position for the carrier, which is usually at the extreme right and left hand ends of the direction of travel.

FIG. 9 shows a cutaway view of the mounting of heads 311, 313 each with a solenoid mounted therein and each with a conduit, 351, 353, respectively projecting through the middle of a solenoid for conducting acoustic waves from a speaker out of a respective gauge head orifice and toward a specimen on the carrier between the two gauge heads. Lines 355, 357 show wires which energize respective solenoids, while other wires, not shown, are connected to respective speakers and microphones for transmitting and receiving acoustic waves.

Figure 10:
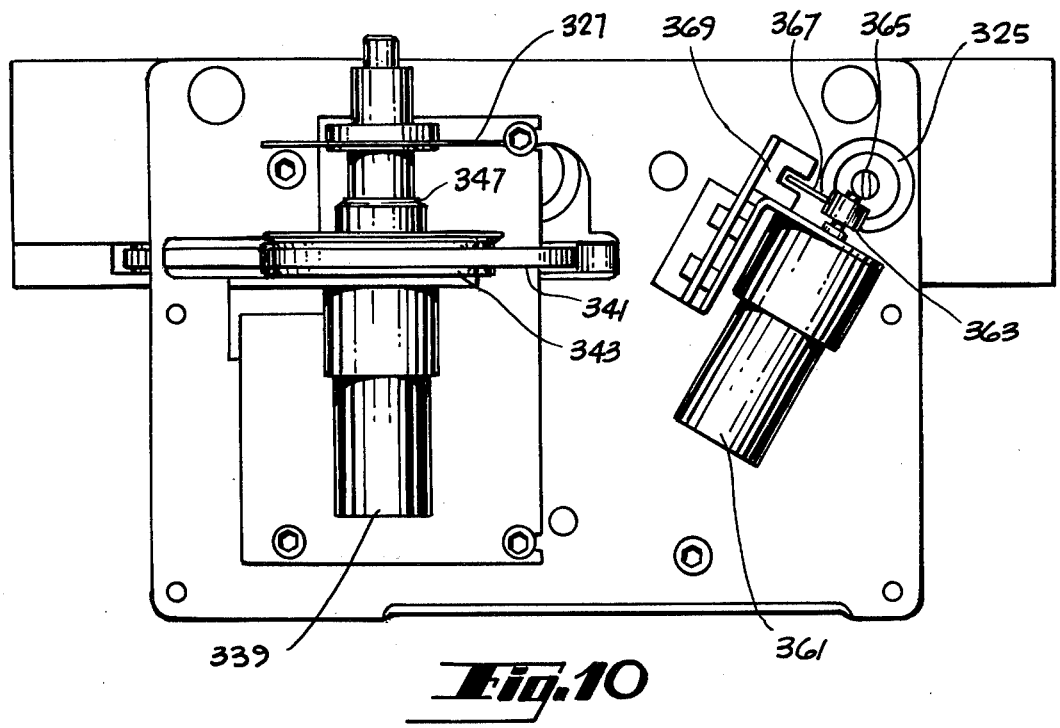
FIG. 10 is a bottom view of the apparatus of FIG. 8.

In the bottom view of FIG. 10, motor 339 is shown driving pulley 343 and belt 341, which in turn is connected to the carrier. The same shaft which drives pulley 343 also drives the opaque limit arm 347, as well as film disk 327.

A second motor 361 is mounted near motor 339 for driving the turntable 325. When measuring the thickness or resistivity of a flat article the carrier takes the article or specimen to be measured between the gauge heads on a linear pass. However, the article to be measured generally has a width dimension, or may be circular as shown in FIG. 8, such that it is desirable to have measurements of thickness and resistivity along different axes. To achieve this, turntable 325 rotates the article being measured a predetermined number of degrees, for example 90 degrees. Motor 361 has a cam 363 which imparts both lifting and rotary motion to a shaft 365 connected to turntable 325. Cam 363 is also connected to an opaque arm 367 which moves through one or more optical switches 369 for indicating the start and stop positions of motor 361. The operation of motor 361 is more clearly illustrated with reference to FIGS. 11, 12 and 13.

With reference to FIg. 11, motor 361 is shown with cam 363 in a rest position whereby the turntable 325 is in its lowermost position and would not be in contact with a wafer or article sitting on the upper surface of a carrier. Cam 363 has a socket which amounts the ball-shaped cam follower 371 which is connected to shaft 365. Cam 363 is also connected to the opaque arm 367 which passes through the optical switch 369.

On command from the film disk, the cam 363 rotates about pivot 373 as shown in FIG. 13. As the cam 363 rotates the cam follower screw 371 causes both upward movement of the turntable 325 as well as rotation. A screw thread in the shank of the cam follower screw 371 in the shaft 365 adjusts the position of turnable 325 below the wafer. Cam follower screw 371 has a ball at its end which can move further into and out of its ball socket 374 in cam 363. The extent of up and down motion of shaft 365 is determined by the dimension of cam 363. The shaft must cause the turntable 325 to clear the carrier. The position of turntable 325 below the wafer determines the extent of rotation of the turntable before it contacts the wafer and afterwards. The shaft 365 will rise, turn and be lowered in a twisting motion indicated by the arrow A in FIG. 12. Some to this twisting motion will occur before and after turntable 325 comes into contact with the wafer that it rotates. the extent of rotation is controlled by the amount of twisting which occurs before and after turntable 325 comes into contact with the wafer which is determined by adjustment of the cam follower screw 371. A preferred pick up point for the wafer is at one half of the vertical travel of the shaft, with a corresponding drop-off point so that 90° rotation of the wafer is achieved for multi-axial test article measurement, as described with reference to FIGS. 20, 21. The upward movement of the turntable gently contacts the wafer, provides rotation, then gently lowers it back onto the carrier.

In FIG. 12, the rising motion of the turntable 325 is seen as the cam 363 rotates in the direction indicated by the arrow B. In FIG. 13, the cam has rotated so that the socket is at its upper extremity and the shaft 365 is about to begin downward motion. As cam rotation continues, the shaft 365 moves downward until motor 361 is stopped by the opaque arm 367 passing through the optical switch 369. The arm 367 overshoots the switch by approximately 10 to 20 degrees so that it rests at the initial position indicated in FIG. 12. The entire process may be repeated until a wafer has been rotated a desired number of times for a preset number of degrees.

With reference to FIG. 14, the action of both motors may be viewed. Pulley 343 is seen to drive belt 341 in a loop so that carrier 315 may be reciprocated. The presence of a wafer or article on the carrier in the limit positions of the carrier, i.e., the load and unload positions, is sensed by the photo diodes 331, 332 which shine into respective phote detectors 333, 335. When the carrier 315 is at its rightmost extremity, as indicated in FIG. 8, the turntable 325 may pass therethrough and lift and rotate a wafer which is placed thereon. Motion is provided by a second motor 361 which is connected to a shaft 365 by means of a cam. The cam provides both lifting and twisting motion to shaft 365 by means of a cam follower. Some lifting and twisting of turntable 325 occurs before and after contact with wafer to be lifted so that although a shaft 365 may rotate by 90 degrees, and back, the amount of wafer rotation depends on how much turntable rotation occurs before and after contact with the wafer. This amount is controlled by a screw 371. The lifting and twisting function of the turntable is useful for taking sample measurements over the surface of a test specimen, such as a wafer as described below with reference to FIGS. 20 and 21.

FIG. 14 also shows a type sensor 381 which is a wire shaped like an inverted V which comes into contact with the bottom side of a wafer. Conductive wire 381 is connected a conductive post 383 and electrically connected as described in FIG. 15 below. Wire 381 has a bias so that it always comes into contact with a wafer passing over it but does not push the wafer out of position nor lift it.

Figure 15:
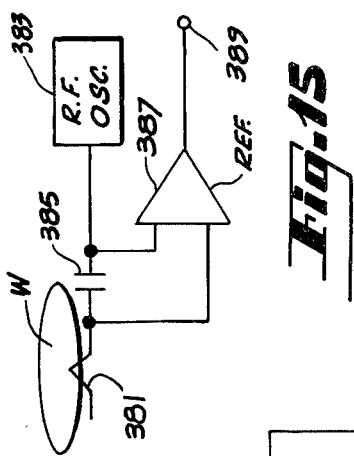
FIG. 15 is a simplified electrical schematic of the wafer type sensor of the present invention.

With reference to FIG. 15 the V-shaped wire 381 is shown to be in physical contact with wafer W. Wafer W is resting on an anodized aluminum carrier so that there is some capacitive coupling between the aluminum of the carrier and the wafer W through the anodized coating. Wire 381 is energized by a radio frequency oscillator 383 which operates at approximately 10 MHz. The r.f. energy from oscillator 383 is fed through a very small capacitor 385 having a value of approximately 50 pf. In operation, the wire 381 and wafer W act as a diode at their contact point. Energy is delivered through capacitor 385 into wire 381 and a charge is built up on capacitor 385 depending on the polarity of the diode junction formed between wire 381 and wafer W. The circuit is completed through the carrier, not shown, which is capacitively coupled to wafer W with the capacitive value being approximately 10 times the capacitive value of the capacitor 385. If the wafer W has one polarity, the capacitor 385 will be charged in one direction, if the wafer W has another polarity, the capacitor 385 will be charged in the opposite direction. The charge on capacitor 385 is sensed by an operational amplifier 387, having a high input impedance, which puts out a positive or negative signal at node 389 with respect to a reference voltage which is supplied to the amplifier. The positive or negative polarity of the wafer indicates its semiconductor type, p or n by means of a corresponding signal at node 389.

To discharge the dielectric coating of the carrier before or after a measurement, a single grounded contact touches the bottom surface of the wafer. Because the wafer being tested has conductivity and the carrier is conductive, the grounded contact between them discharges the charge on the coating in the same way a bleeder resistor operates. During a measurement, the r.f. path through capacitor 385 is the major current path and the path through the grounded contact is not significant.

In FIG. 15a, the electrical configuration of FIG. 15 may be viewed in more detail. The R.F. oscillator enclosed within dashed line 383 may be seen to comprise a transistor 350 connected as an oscillator whose frequency is controlled by a crystal 352 connected between the base and collector thereof. Crystal control is not necessary, but merely preferred. Suitable load members 354 are used to complete the oscillator circuit. The oscillator 383 is keyed by a control signal applied to terminal 356 connected to the base of transistor 350. The control signal is applied for the duration of a measurement. For example, the control signal may be applied when an infrared sensor detects that the wafer is in position and then shut off after the measurement. A transistor amplifier, within the dashed line 358, of the emitter follower type, amplifies the output of oscillator 383 and sends the amplified R.F. signal through capacitor 385 to the V shaped first conductive wire 381 which makes contact with wafer W.

All materials in this instrument, including the carrier 315 and first wire 381 are made of materials which will not diffuse into the wafer when in contact therewith. For this reason, first wire 381 is made of tungsten and the carrier 315 is made of anodized aluminum with the anodized coating 360 forming a dielectric barrier between the aluminum base portion 362 of the carrier and the wafer W which is placed on top of the anodized layer and in contact with wire 381. Parasitic capacitance built up between the wafer and the aluminum portion 362 of the carrier is discharged through a second conductive wire 364, connected to ground at one end and positioned so that its free end contacts wafer W, but not first wire 381. The second wire 364 acts as a bleeder resistor, as mentioned previously.

When resistivity type of a wafer is measured by applying a signal to terminal 356 which turns on transistor 350, the capacitor 385 is charged with a polarity depending on the positive or negative polarity type of the wafer because of the point contact diode formed between the wire 381 and the wafer itself. This p-n junction between the wire 381 and wafer W rectifies the radio frequency current coming through capacitor 385 and thus charges the capacitor to a positive or negative polarity at node 364. The charge at node 364 is sensed by the operational amplifier and its ancillary components enclosed by the dashed line 387. That amplifier includes an integrated circuit operational amplifier 374 which may be for example, type CA 3140, which has an inverting input terminal 376 connected to a negative supply so that the amplifier output at terminal 389 is usually positive, except when a negative wafer is detected. A negative wafer causes a negative signal to be detected at the non-inverting input 378 which is amplified and transmitted to the output terminal 389. Resistors 380 establish a proper working point for the amplifier 374, while diodes 379 form a large resistance for biasing the operational amplifier input with respect to ground.

During the time of the measurement, the parasitic capacitance C between the base 362 of the carrier and wafer W is charging, as is capacitor 385. After a measurement, but before a wafer is removed, the parasitic capacitor C is discharged through second tungsten conductive wire 364. The same occurs when a wafer is first placed on the carrier, before a measurement. A wafer which may have electrostatic charge thereon is discharged through second wire 364.

With reference to FIGS. 8 and 14, it will be noted that the wafer W is loaded onto the carrier at a position removed from the first wire 381. In other words, the first wire 381 is fixed at a position beneath the gauge heads. However, the second wire 364 is connected to the base 362 of the carrier at the load station where a wafer is placed. By this arrangement, the second wire 364 has an opportunity to remove charge from wafer W and after a measurement.

The circuit of FIG. 15a is used together with the resistivity gauge of the present invention in order to further characterize the physical properties of a semiconductor wafer when a semiconductive material is being measured. However, the circuit has independent utility and could be made into a separate and distinct instrument in its own housing. Such a separate instrument would require that a keying signal be applied to transistor 350, but this could be done manually, such as by pushing a button when a measurement is desired.

Exemplary housings for such a separate instrument are shown in FIGS. 15b and 15c. With respect to FIG. 15b, the housing is a box-like chassis having the first wire 381 projecting from a slot 382 that a wafer W on a wafer feeding member 384 moving in the direction of arrow H will come into contact with the first wire 381. Wafer feeding member 384 could be made similar to carriage 315 in FIG. 7. The second wire 364 projects through a separate aperture 366 with the first and second wires 381, 364 making contact with the underside of wafer W. A measurement of wafer type is made by keying the transistor oscillator by manual means, such as a push button 368. A visual indication of wafer type may be read on a visual display 380. It will be realized that the wire 364 is grounded to the anodized aluminum chassis 360 which is in capacitive relation to the wafer W since the anodized coating forms a dielectric between the wafer and the aluminum layer below it.

In FIG. 15c, a hand held gauge is shown for measuring wafer p or n type, either while a wafer is supported on carriage 315 of FIG. 7, or at other times, such as in wafer shipping trays or other holders. The hand held unit resembles a soldering gun in which the forewardly projecting wire 381 is a fine wire made of a material which will not diffuse into the wafer. Like a soldering gun, the body 390 has a trigger or button 394 for energizing the circuit shown in FIG. 15a. The wire 381 is intended to make contact with one side of a wafer, such as held in transporting device 388 wherein a measurement is made. The measurement is made by keying the transistor oscillator by means of the trigger 394 and obtaining a determination of p or n type in a visual display, for example two light emitting diodes 392 which may indicate either wafer type. The apparatus may be powered by battery supplies, as is customary for many integrated circuit products.

Figure 16:
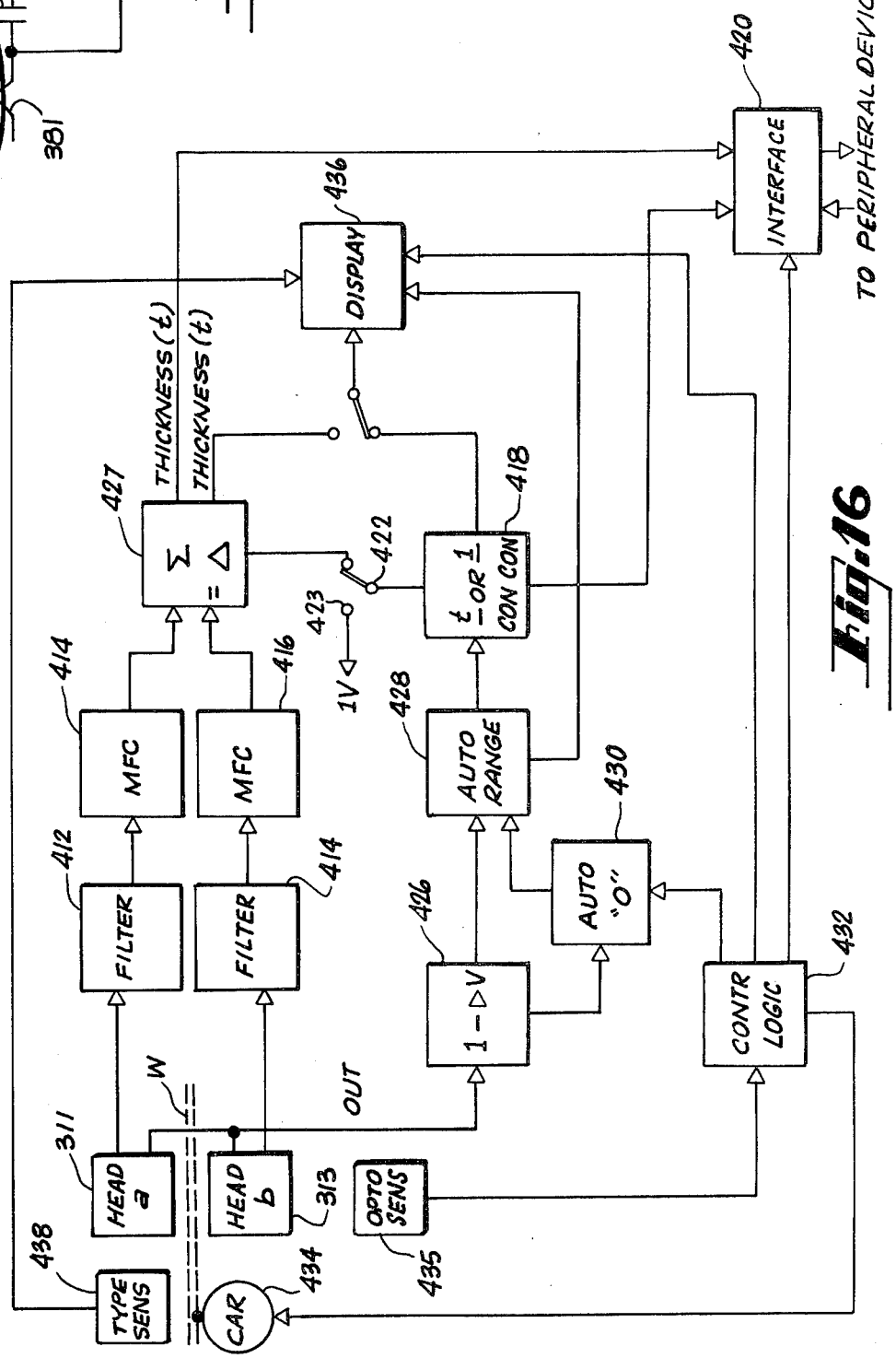
FIG. 16 is an electrical block diagram for the resistivity gauge of the present invention.

With reference to FIG. 16, a pair of gauge heads 311, 313 are spaced on opposite sides of a wafer W. Each of the heads produces a signal due to acoustic pressure between the head and the wafer as described with reference to FIG. 6. Those signals, are transmitted along wires 312, 314 and filtered in filters 412, 414 and then transmitted to the multifunction converters 414, 416, respectively. The two signals are then combined representing the two distances from each head to a front planar surface of a wafer or the like. This combined distance is subtracted from the spacing between the heads to yield a thickness signal. The combining of the two signals takes place in block 427, corresponding to the sum and different networks 122 and 125 of FIG. 6. The thickness signal is transmitted to another multifunction converter 418 and to interface 420. The connection to multifunction converter 418 is made through switch 422 which has available to it a unit voltage reference as an alternative to the signal from network 427. If connected to the unit reference voltage, the instrument reads sheet resistance (ohms per square unit of area). If connected to the network 427, the instrument reads bulk resistivity (ohms-cm.).

Besides providing acoustic pressure signals, the gauge heads 311, 313 provide an eddy current signal indicative of the resistivity of the wafer. This current is transmitted to the voltage converter 426 which provides a voltage proportional to the eddy current input thereto. The voltage signal is then transmitted to an automatic setting range circuit 428. This circuit is desirable because the gauge of the present invention displays only three digits of information, as shown in FIG. 7, although a larger display could be used. However, a larger display need not be used if an automatic range adjustment is used. Briefly, this circuit sets the size of the denominator used in the multifunction converter 418 by selection of significant digits. Automatic range circuits are known in the art, particularly where digital displays are used. The auto range circuit has two internal voltage comparators which look at the input signal and essentially moves decimal positions so that significant digits appear in the display.

The resistivity signal of the current-to-voltage converter 426 is also supplied to an automatic zeroing circuit 430 which causes the measurement of resistivity to be made between the carrier in its empty position and the carrier with the wafer loaded therein. The reason for doing this is that eddy current measurements are not temperature stable and slight temperature variations can cause a problem. Moreover, eddy current measurements also depend on the gap separation. In the present case, this separation may vary over a period of time and hence the automatic zeroing circuit tends to eliminate periodic drift.

The difference between the loaded and unloaded carrier is sensed by optical sensors 435 which are connected to control logic 432. The control logic 432 performs the following functions: it reads the film disk thereby starting the measurement cycle, repeating it if commanded, and stopping it. Within the measurement cycle the thickness and resistivity transducers are energized and manually selected output signals are displayed. For silicon wafers, conductivity type is determined. Further, the control logic interprets optical signals from the optical sensors to determine carrier and turntable position. From these positions and from film disk and manual commands, the control logic controls carrier and turntable motion. Control logic 432 is connected to display unit 436 for enabling information to be displayed. That information may come either from the auto range circuit 428, from the multifunction converter 418 or the arithmetic network 427, or from the wafer type sensor 438. The latter sensor was described in FIG. 15 and provides an indication whether the wafer under test is of p or n type.

The multifunction converter 418 may take the unit reference voltage from node 423 and divide it by conductance obtained from the two gauge heads. This division yields a sheet resistance signal which may be displayed on the display 436. On the other hand, if switch 422 is connected to network 427 the thickness t of wafer W is obtained for division by conductance to obtain resistivity. Both the thickness and the resistivity outputs are connected to an interface circuit 420 which provides an output to a computing device or a display device 436.

Solenoids 74, 76 in FIG. 5 were described as single solenoidal coils each in parallel with a capacitor used in resonant or tank circuits having a high Q. Since the present invention is used to measure the conductivity of semiconductor wafers, although use is not limited to such wafers, variations in conductivity are encountered among various specimens to be measured. This implies that the inductive coupling between the coils and the test specimen will vary. The apparatus of the present invention will span five decades of resistivity using the tank switching arrangement described with reference to FIG. 17.

In general, inductive penetration through the test article must be good, preferably to a distance about ten times greater than the measured thickness. More conductive wafers permit less penetration than less conductive wafers. To handle test specimen resistivity ranging from 0.001 ohm-cm. to 100 ohm-cm. two resonant frequencies are used for the axial magnetic field generated by the solenoids to control skin depth penetration and two separate turns ratios are used in the solenoids to vary the inductive coupling. Fewer turns causes better coupling; more turns less coupling. For example, with highly conductive wafers, less coupling is desired, together with increased penetration. To accomplish this, more turns are used in the solenoid at a lower frequency, since lower magnetic field frequencies increase skin depth penetration.

FIG. 17 shows the lower gauge head having coils 451, 453 and the upper gauge head having coils 457, 459. The lower and upper gauge heads face a specimen to be tested, placed in the plane indicated by dashed line 450. The coils can be selectively connected by a gang connection 465 joining single pole, double throw switches 461, 463, and 467, termed coil switches. Another switch 469, connected to gang connection 465, termed a capacitor switch, selectively connects or switches capacitor 471 in parallel with the supplemental capacitor bank 473. In one switch position, the one shown in FIG. 17, input energy applied to input terminal 475 will energize coil 459, a low turn coil, in the upper head, 451 in the lower head, another low turn coil, which is in series with the former, as well as capacitor 471, an 82 pf. capacitor arranged in parallel with the two coils. The resonant frequency of the tank is on the order of 0.1 MHz which is suitable for measuring wafers with sheet resistance ranging from 0.01 ohms per square to 10 ohms per square.

When the switches are thrown to the opposite position to that shown in FIG. 17, all of the coils 451, 453, 457 and 459 are energized and the parallel capacitor bank 473 is placed in parallel with capacitor 471. The coils 453, 451 are multi-turn coils and the capacitance of capacitor bank 473 is approximately 0.03 uf, although capacitor values are only exemplary and not required values. The resonant frequency of this tank circuit is on the order of 10 MHz which is suitable for measuring wafers with sheet resistance ranging from 10 ohms per square to 2000 ohms per square. The output signal from the network of FIG. 17 is taken at terminal 477.

FIG. 18 shows a ferrite cup 76, as used in a gauge head 61 in FIG. 5. However, rather than using a single solenoidal coil, paired coils 451 and 453 are used as described with reference to FIG. 17. Both coils are coaxially wound on a common annular ferrite bobbin 481 which fits into the annular ferrite cup 76 with the coils. A slot 483 in the side of the cup allows leads from the coils to emerge from the side of the cup. The bobbin is adhesively secured in the cup with the multi-turn coil 453 nearest the position of a test specimen. FIG. 19 shows that multi-turn coil 453 occupies half the height of the bobbin 481 with smaller diameter wire, while coil 451 having few turns has larger diameter wire to occupy the other half of the bobbin height.

Use of the two coils as the solenoid means for generating an axial magnetic field perpendicular to a test material increases the range of resistivity and conductance which can be measured. A simple manual toggle on the back of the instrument illustrated in FIG. 7 controls the ganged connection 465 of switches 461, 463, 467 and 469.

In using the instrument of the present invention, it is often desirable to sample conductivity at various points on a test specimen, such as a semiconductor wafer. Test specimens may have variable thicknesses or electrical properties which can cause nonuniform measurements from point to point on a test object. FIG. 20 includes a top schematic view of the apparatus of the present invention, including the cantilever arm 323 which supports a gauge head. Also shown is the article carrier 309, supporting a wafer W, or similar article. The wafer W is shown in the load position 411. The film disk described with reference to FIGS. 8 and 9 commands the carrier 309 to successively advance the wafer W to the positions marked 1, 2 and 3, stopping at each position to make a measurement of conductivity. On reaching position 3, the carrier is commanded to stop, retreat to the loading position 411, rotate the wafer or test article by 90 degrees, then advance the wafer to fourth and fifth measurement positions corresponding to the first and third positions where additional measurements are made. Lastly, the wafer is moved to an unloading position 413. The loading and unloading positions 411 and 413 are such that a wafer or test article will clear the cantilever arm 323 when lifted. FIG. 20 shows a reference specimen 415 positioned on an edge of the carrier for movement beneath cantilever arm 323 between test article measurements. Reference specimen measurement may be commanded by a film disk, or manually.

The sampling plan described with reference to FIG. 20 will result in measurements indicated in FIG. 21. In this figure, the points on the surface of the wafer W indicate regions where measurements were made using the operating plan of FIG. 20. There is no need for the measurement to be limited to any particular number or location of points. Sampling points may be taken along several axes, with the degree of rotation of the turntable supporting the wafer W being controlled by a screw, as described with reference to FIGS. 11-13. Each point indicates a surface location where a thickness measurement has been made and immediately thereafter conductivity was computed based on a resistivity measurement which is combined with article thickness, as described,

What is claimed is:

1. A non-contacting resistivity gauge for magnetically susceptible sheet material comprising,
    first and second gauge heads mutually spaced a distance relative to the opposite sides of a magnetically susceptible sheet material whose resistivity is to be measured, each gauge head having acoustic pressure means including a speaker and a microphone disposed in the portion of the gauge head facing the sheet material and having an acoustic pressure communication zone therebetween for producing a first electrical signal, the first electrical signals from the first and second gauge heads electrically combined to be representative of the thickness of said sheet material, each gauge head further having solenoid means generating an axial magnetic field zone which is generally perpendicular to said sheet material and in magnetic induction relation therewith for producing a second electrical signal, the second electrical signals from the first and second gauge heads electrically combined to be representative of the conductance of said sheet material, said solenoid means surrounding at least a portion of said acoustic pressure means, with said acoustic pressure communication zone coinciding with the axial magnetic field zone, such that the areas over which said conductivity and thickness measurements are made are the same, and
    electrical circuit means for combining said first and second electrical signals yielding a third electrical signal representative of resistivity of said sheet material.

2. The apparatus of claim 1 wherein each gauge head has said speaker and microphone mounted inside of said gauge head, both communicating with said sheet material through said solenoid means, said solenoid means mounted in said gauge head proximate to said sheet material.

3. The apparatus of claim 1 wherein each gauge head has said speaker and microphone mounted inside of said gauge head communicating with said sheet material through a pair of non-magnetic tubes, one inside of the other, but disposed within said solenoid means, said solenoid means mounted in said gauge head proximate to said sheet material 4. The apparatus of claim 1 wherein said solenoid means comprises a solenoidal coil housed in a ferrite core, the solenoid means of said first and second gauge heads being axially aligned.

5. The apparatus of claim 4 wherein said core is annular having a U-shaped section generating the annulus.

6. The apparatus of claim 1 wherein a capacitance shield is interposed between each of said solenoid means and said sheet material in said axial magnetic field, said capacitance shield comprising a grounded conductive planar member disposed generally perpendicular to said axial magnetic field, said planar member having a plurality of radial slits therein extending outwardly from the axis of said axial magnetic field for preventing magnetic induction of eddy currents therein, but conducting capacitive currents to ground thereby providing capacitive shielding.

7. The apparatus of claim 1 wherein each gauge head is cylindrical and has a discoidal capacitance shield thereover facing said sheet material, said capacitance shield comprising a grounded conductive planar member disposed generally perpendicular to said axial magnetic field, said planar member having a plurality of radial slits therein extending outwardly from the axis of said axial magnetic field for preventing magnetic induction of eddy currents therein, but conducting capacitive currents to ground thereby providing capacitive shielding.

8. The apparatus of claim 6 wherein said capacitance shield is less than 10 mils thick.

9. The apparatus of claim 6 wherein said radial slits are less than 10 mils wide.

10. The apparatus of claim 6 wherein said radial slits extend outwardly from a central hole through which acoustic pressure communication is maintained with said gauge head.

11. The apparatus of claim 1 further defined by an article carrier adapted for supporting sheet material to be measured, said article carrier mounted for linear motion proximate to said first and second gauge heads bringing articles to be measured into magnetic induction communcation with said gauge heads.

12. The apparatus of claim 11 whereby said article carrier encompasses said gauge heads, said carrier having a carrier surface spaced relative to said gauge heads so that an article on said carrier passes between said gauge heads.

13. The apparatus of claim 11 whereby said article carrier is connected to a motor with means for reciprocal motion.

14. The apparatus of claim 13 whereby said means for reciprocal motion includes a film element having opaque and transparent regions and optical switch means for reading said regions.

15. The apparatus of claim 11 further defined by means associated with said carrier for rotating articles disposed on said carrier.

16. The apparatus of claim 15 whereby said means for rotating flat articles comprise a turntable disposed below said carrier, said turntable connected to motor means for elevating and rotating said turntable.

17. The apparatus of claim 16 wherein said turntable includes means for varying the amount of rotation of an article disposed on said carrier.

18. The apparatus of claim 11 further comprising means for obtaining said conductance signal as a difference in conductance between the carrier supporting sheet material and not supporting sheet material.

19. The apparatus of claim 1 wherein said solenoid means is connected to at least one capacitor forming a tank circuit whereby said axial magnetic field has a frequency associated with the resonant frequency of said tank circuit.

20. The apparatus of claim 19 wherein the solenoid means of each gauge head comprises at least one pair of solenoidal coils electrically connected through a coil switch so that different combinations of coils of said first and second gauge heads may be selected.

21. The apparatus of claim 20 further defined by said coils of each gauge head being coaxially wound on a common bobbin, said bobbin disposed in a ferrite core.

22. The apparatus of claim 20 further defined by supplemental capacitors electrically connected through a capacitor switch to said one capacitor so that different combinations of capacitors may be selected.

23. The apparatus of claim 20 wherein the solenoid means of each gauge head are axially aligned.

24. A method for measuring resistivity of magnetically susceptible sheet-like articles, such as semiconductor wafers and the like, of unknown thickness comprising,
 (i) measuring the thicknes of a magnetically susceptible sheet-like article, by the steps comprising,
  (a) directing acoustic energy at opposed sides of a sheet-like article of known thickness from aligned sources on opposite sides of said article, each of said sources having a surface proximate to the article defining a gap therebetween,
  (b) simultaneously detecting said acoustic energy in the gap on each side of the article and producing a pair of first electrical signals in response thereto,
  (c) generating a second pair of electrical signals representing acoustic energy output from said sources,
  (d) combining respective first and second electrical signals of each pair of signals with a respective reference signal in accord with a known relation to yield first and second output signals respresenting gaps on each side of said article,
  (e) repeating steps (a)–(d) for a sheet-like article of unknown thickness, and
  (f) adding the first and second output signals representing the gaps on each side of said article of known thickness with a signal representing the thickness of said article of known thickness and subtracting therefrom first and second output signals representing the gaps on each side of said article of unknown thickness, the remainder converted to an output signal representing the unknown thickness of said sheet-like article,
 (ii) measuring the conductance of said sheet-like article by generating axial solenoidal magnetic fields generally perpendicular to the sheet material and on opposed sides of the article, the zones of the magnetic fields and the acoustic energy mutually coinciding, such that the areas over which said conductivity and thickness measurements are made are the same, and producing an electrical signal representing said conductance,
 (iii) dividing said thickness signal by said conductance signal to yield a signal representing the resistivity of said sheet-like article.

25. A transducer assembly for use in measuring resistivity in magnetically susceptible sheet material comprising,
first and second gauge heads mutually spaced a known distance relative to the opposite sides of a magnetically susceptible sheet material whose resistivity is to be measured, each gauge head having acoustic pressure means including a speaker and a microphone disposed in the portion of the gauge head facing the sheet material and having an acoustic pressure communication zone therebetween for measuring thickness of said sheet material, each gauge head further having electrical solenoid means generating an axial magnetic field zone which is generally perpendicular to said sheet material and in magnetic induction relation therewith for measuring conductance of said sheet material, said solenoid means surrounding at least a portion of said acoustic pressure means, with said acoustic pressure communication zone coinciding with the axial magnetic field zone, such that the areas over which said conductivity and thickness measurements are made are the same.

26. The apparatus of claim 25 wherein each gauge head has a speaker and microphone mounted inside of said gauge head communicating with said sheet material through at least one non-magnetic tube disposed within said solenoid means, said solenoid means mounted in said gauge head proximate to said sheet material.

27. The apparatus of claim 25 wherein each gauge head has said speaker and microphone mounted inside of said gauge head communicating with said sheet material through a pair of non-magnetic tubes, one inside of the other, both disposed within said solenoid means, said solenoid means mounted in said gauge head proximate to said sheet material.

28. The apparatus of claim 25 wherein said solenoid means comprises a solenoidal coil housed in a ferrite core, the solenoid means of said first and second gauge heads being axially aligned.

29. The apparatus of claim 25 wherein said core is annular having a U-shaped section generating the annulus.

* * * * *

UNITED STATES PATENT AND TRADEMARK OFFICE
CERTIFICATE OF CORRECTION

PATENT NO. : 4,302,721

DATED : November 24, 1981

INVENTOR(S) : Karel Urbanek, George J. Kren and William R. Wheeler

It is certified that error appears in the above-identified patent and that said Letters Patent are hereby corrected as shown below:

| | |
|---|---|
| Col. 4, line 16 | "of the land" should read --of the head-- |
| Col. 7, line 46 | "layer of polyester" should read --layer on polyester-- |
| Col. 14, line 52 | "which amounts the ball-shaped cam" should read --which mounts the ball-shaped cam-- |
| Col. 15, line 3 | "Some to this" should read --Some of this-- |
| Col. 15, line 5 | "the extent of" should read --The extent of-- |
| Col. 15, line 43 | "contact with wafer" should read --contact with the wafer-- |
| Col. 15, line 55 | "connected a conductive post" should read --connected to a conductive post-- |
| Col. 17, line 37 | "and after a measurement" should read --before and after a measurement-- |
| Col. 17, line 51 | "that a wafer W" should read --such that a wafer W-- |
| Col. 18, line 11 | "of p or n type" should read --of the p or n type-- |

UNITED STATES PATENT AND TRADEMARK OFFICE
CERTIFICATE OF CORRECTION

PATENT NO. : 4,302,721

DATED : November 24, 1981

INVENTOR(S) : Karel Urbanek, George J. Kren and William R. Wheeler

It is certified that error appears in the above-identified patent and that said Letters Patent are hereby corrected as shown below:

Claim 24, (d)   col. 23, lines 39 and 40 "respresenting" should read --representing--

Claim 26   col. 24, line 35 "has a speaker" should read --has said speaker--

Signed and Sealed this

Eighth Day of March 1983

[SEAL]

Attest:

GERALD J. MOSSINGHOFF

Attesting Officer   Commissioner of Patents and Trademarks